US012778595B2

(12) United States Patent
Kawamura

(10) Patent No.: US 12,778,595 B2
(45) Date of Patent: Nov. 3, 2026

(54) HEMOSTATIC DEVICE

(71) Applicant: TERUMO KABUSHIKI KAISHA, Tokyo (JP)

(72) Inventor: Tomoya Kawamura, Aliso Viejo, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 267 days.

(21) Appl. No.: 18/468,222

(22) Filed: Sep. 15, 2023

(65) Prior Publication Data

US 2024/0000462 A1 Jan. 4, 2024

Related U.S. Application Data

(63) Continuation of application No. PCT/JP2022/015311, filed on Mar. 29, 2022.

(30) Foreign Application Priority Data

Mar. 30, 2021 (JP) ................................. 2021-057231

(51) Int. Cl.
*A61B 17/135* (2006.01)
*A61B 17/132* (2006.01)
(Continued)

(52) U.S. Cl.
CPC .. *A61B 17/135* (2013.01); *A61B 2017/00659* (2013.01); *A61B 2017/12004* (2013.01); *A61B 17/1325* (2013.01)

(58) Field of Classification Search
CPC ........ A61B 17/135; A61B 2017/00659; A61B 2017/12004; A61B 17/1325
See application file for complete search history.

(56) References Cited

U.S. PATENT DOCUMENTS

2004/0049214 A1 3/2004 Akerfeldt
2004/0098035 A1* 5/2004 Wada .................. A61B 17/135 602/76

(Continued)

FOREIGN PATENT DOCUMENTS

DE 10054188 A1 5/2002
JP 2021502220 A 1/2021

(Continued)

OTHER PUBLICATIONS

Extended European Search Report dated Jun. 14, 2024, issued in corresponding European Application No. 22780867.2. (10 pages).

(Continued)

*Primary Examiner* — Jing Rui Ou
(74) *Attorney, Agent, or Firm* — BUCHANAN INGERSOLL & ROONEY PC

(57) ABSTRACT

Provided is a hemostatic device capable of effectively applying a compressive force to a puncture site formed at a predetermined position avoiding a metacarpal bone of an index finger of a hand and a metacarpal bone of a thumb of the hand even when hemostasis is performed on the puncture site. The hemostatic device includes a support member configured to cover the first puncture site, a securing member configured to secure the support member to the first puncture site, and an inflatable member connected to the support member and configured to compress the first puncture site. The support member has rigidity higher than rigidity of the inflatable member. A width of the support member becomes shorter from an upper end portion toward a lower end portion. A thickness of a side surface portion of the support member becomes thinner from the upper end portion toward the lower end portion.

20 Claims, 20 Drawing Sheets

(51) Int. Cl.
*A61B 17/00* (2006.01)
*A61B 17/12* (2006.01)

(56) References Cited

U.S. PATENT DOCUMENTS

| | | | | |
|---|---|---|---|---|
| 2015/0018869 | A1* | 1/2015 | Benz | A61B 17/135 606/203 |
| 2015/0335334 | A1* | 11/2015 | Pancholy | A61B 5/0295 606/202 |
| 2016/0206298 | A1* | 7/2016 | Keene | A61B 17/0057 |
| 2018/0014831 | A1* | 1/2018 | Salimi | A61B 17/135 |
| 2019/0133602 | A1* | 5/2019 | Kiemeneij | A61B 17/1325 |
| 2019/0314035 | A1 | 10/2019 | Hopkinson et al. | |
| 2021/0145452 | A1 | 5/2021 | Hioki et al. | |

FOREIGN PATENT DOCUMENTS

| | | | |
|---|---|---|---|
| WO | 2020027122 | A1 | 2/2020 |
| WO | 2020111184 | A1 | 6/2020 |

OTHER PUBLICATIONS

International Search Report (PCT/ISA/210) with translation and Written Opinion (PCT/ISA/237) mailed on May 17, 2022, by the Japanese Patent Office as the International Searching Authority for International Application No. PCT/JP2022/015311. (10 pages).

* cited by examiner

HEMOSTATIC DEVICE

CROSS-REFERENCES TO RELATED APPLICATIONS

This application is a continuation of International Patent Application No. PCT/JP2022/015311 filed on Mar. 29, 2022, which claims priority to Japanese Patent Application No. 2021-057231 filed on Mar. 30, 2021, the entire content of both of which is incorporated herein by reference.

TECHNOLOGICAL FIELD

The present invention generally relates to a hemostatic device.

BACKGROUND DISCUSSION

As one of catheter procedures, a procedure is known in which various medical elongated bodies are introduced into a blood vessel of a limb such as an arm or hand of a patient through a puncture site formed by puncturing the blood vessel to perform treatment and therapy on a lesion site. For example, U.S. Patent Application Publication No. 2019/0133602 discloses a hemostatic device for hemostasis on a puncture site formed to enable access to a blood vessel (including a distal radial artery) running in a hand.

The hemostatic device in U.S. Patent Application Publication No. 2019/0133602 includes: a pressing member that applies a compressive force to a puncture site (hereinafter, also simply referred to as a "puncture site") formed in a hand of a patient; a band body that secures the pressing member to the hand of the patient; and a support member that is disposed on the band body and presses the pressing member against the hand of the patient. In addition, the band body includes a first band body disposed between fingers of the patient and a second band body wrapped at a position on a forearm side of the hand of the patient.

SUMMARY

An operator such as a doctor (hereinafter referred to as an "operator") may set the puncture site at a predetermined position avoiding a metacarpal bone of an index finger of the hand and a metacarpal bone of a thumb of the hand when forming the puncture site on the hand. By setting the puncture site at such a predetermined position, the operator can prevent a puncture device such as an indwelling needle from interfering with the metacarpal bone of each finger when forming the puncture site.

However, in a case where the puncture site is formed at the predetermined position avoiding the metacarpal bone of the index finger and the metacarpal bone of the thumb, when hemostasis is performed using the hemostatic device described in U.S. Patent Application Publication No. 2019/0133602, the following problems occur.

The operator disposes the pressing member and the support member of the hemostatic device in the above-described U.S. application publication so as to overlap the puncture site when the hemostasis is performed on the puncture site.

When the operator disposes the hemostatic device in the above-identified U.S. application publication on the hand of the patient, the support member may be placed on the metacarpal bone of the index finger and the metacarpal bone of the thumb. In the hemostatic device in the above-identified U.S. application publication, when the second band body is wrapped around the hand of the patient in a state where the support member is disposed on the hand of the patient as described above, a gap is formed between the pressing member and the hand, and the second band body does not fit along an outer periphery of the hand of the patient. In such a state, the pressing member and the support member can be firmly secured to the hand of the patient by strongly tightening the first band body of the hemostatic device in the above-identified U.S. application publication. Meanwhile, in such a case, since it is necessary to strongly tighten the first band body of the hemostatic device in the above-identified U.S. application publication, pain may occur in the patient. Therefore, in the hemostatic device in the above-identified U.S. application publication, when the first band body cannot be strongly tightened due to pain or the like of the patient, the support member is disposed in a state of being inclined in a direction approaching a body surface of the hand from a fingertip side of the hand toward the forearm side. In the hemostatic device in the above-identified U.S. application publication, when the support member is disposed as described above, the pressing member cannot apply a compressive force to the puncture site in a vertical direction. Accordingly, the hemostatic device in the above-identified U.S. application publication cannot effectively apply the compressive force to the puncture site.

The hemostatic device disclosed here is capable of effectively applying a compressive force to a puncture site formed at a predetermined position avoiding a metacarpal bone of an index finger of a hand and a metacarpal bone of a thumb of the hand even when hemostasis is performed on the puncture site.

A hemostatic device according to one aspect includes: a support member configured to cover a puncture site formed in a patient; a securing member configured to secure the support member to the puncture site of the patient; and a pressing member connected to the support member and configured to compress the puncture site of the patient, in which the support member includes an upper end portion that is located on a distal side of the pressing member and forms an end portion of the support member, a lower end portion that is located on a proximal side of the pressing member and forms an end portion on a side opposite to the upper end portion, and a side surface portion that connects the upper end portion and the lower end portion, the support member has rigidity higher than that of the pressing member, the securing member includes a first band body portion configured to be disposed between fingers of the patient and extending in a first direction, and a second band body portion extending in a second direction different from the first direction, the support member is configured such that a width of the support member becomes shorter from the upper end portion toward the lower end portion and a thickness of the side surface portion becomes thinner from the upper end portion toward the lower end portion, the first band body portion extends in the first direction from the upper end portion side, and the second band body portion extends in the second direction from the side surface portion side.

The above hemostatic device includes the support member having rigidity higher than that of the pressing member. The support member is disposed so as to cover the puncture site together with the pressing member when hemostasis is performed on the puncture site formed at a predetermined position avoiding a metacarpal bone of an index finger of a hand of a patient and a metacarpal bone of a thumb of the hand of the patient. The support member can prevent the pressing member from lifting from the hand of the patient by pressing the pressing member against the hand of the patient. In addition, the width of the support member becomes shorter from the upper end portion toward the lower end portion. Therefore, when the support member is disposed on the hand of the patient, the support member can be disposed along the metacarpal bone of the index finger and the metacarpal bone of the thumb. Therefore, in the above hemostatic device, the second band body portion can be firmly wrapped along an outer periphery of the hand of the patient. In addition, in the support member, the thickness of the side surface portion becomes thinner from the upper end portion toward the lower end portion. In addition, the first band body portion configured to be disposed between fingers of the patient is configured to extend from the upper end portion side of the support member and press the upper end portion side of the support member against the hand of the patient. Therefore, the pressing member can apply a force to one end portion of the support member when the hemostasis starts in a state where the hemostatic device is attached to the hand of the patient. The one end portion side of the support member is lifted by the force applied by the pressing member. Accordingly, the support member is disposed such that a lower surface of the support member is substantially parallel to a body surface of the hand of the patient. Therefore, in the hemostatic device, the compressive force of the pressing member can be directed in a direction perpendicular to the puncture site by securing the first band body portion and the second band body portion to the hand of the patient in a state where the pressing member and the support member are disposed at the puncture site. Accordingly, the hemostatic device can effectively apply the compressive force to the puncture site.

According to another aspect, a hemostatic device securable to a hand of a patient comprises: a covering portion positionable in overlying relation to a puncture site on the hand of the patient when the hemostatic device is secured to the hand of the patient, with the covering portion including an inner surface configured to face toward the patient's hand when the hemostatic device is secured to the hand of the patient. A first band body portion and a second band body portion are provided for securing the covering portion to the patient's hand, with the first band body portion being fixed to the covering portion, extending away from a first part of the covering portion in a first direction of extent and configured to be positioned between fingers of the patient's hand, and the second band body portion being fixed to the covering portion and extending away from a second part of the covering portion in a second direction of extent different from the first direction of extent, wherein the first part of the covering portion is spaced from the second part of the covering portion. A pressing member is expandable to apply a compressive force to the puncture site when the hemostatic device is secured to the hand of the patient, with the covering portion overlying the pressing member. A support member is positioned between the covering portion and the pressing portion so that the covering member overlies the support member and the support member overlies the pressing member, with the support member being more rigid than the pressing member. The support member includes a first end portion and a second end portion that are disposed at opposite sides of the support member in a plan view of the support member, with the first end portion of the support member facing towards the first part of the covering portion and being located closer to the first part of the covering portion than the second end portion of the support member, and the second end portion of the support member facing away from the first part of the covering portion. The thickness of the first end portion of the support member is greater than the thickness of the second end portion of the support member.

In accordance with another aspect, a method comprises: positioning an expandable pressing member on a patient's hand, wherein a covering portion is positioned in overlying relation to the pressing member with a first band body portion, a second band body portion and a third band body portion fixed to the covering portion and extending away from the covering portion in different directions. The first band body portion, the second band body portion and the third band body portion each include a first surface and a second surface that face in opposite directions, with the first surfaces of the first band body portion, the second band body portion and the third band body portion facing in a common direction when the hemostatic device is laid flat. The second surfaces of the first band body portion, the second band body portion and the third band body portion facing in a common direction when the hemostatic device is laid flat. The first surface of the first band body portion and the second band body portion each include a securing portion, and the second surface of the second band body portion and the second surface of the third band body portion each include a securing portion. The securing portion on the second surface of the third band body portion includes first and second branch portions that are spaced apart from one another along at least a portion of a longitudinal extent of the first and second branch portions of the securing portion. The method additionally comprises positioning the pressing member in overlaying relation to either a first puncture site of the patient's hand or a second puncture site of the patient's hand, with the second puncture site being spaced from the first puncture site, and securing the pressing portion and the covering portion to the patient's hand. The securing of the pressing portion and the covering portion to the patient's hand comprises: wrapping the third band body portion and the second band body portion around a portion of the patient's hand and mating the securing portion on the first surface of the second band body portion with the first branch portion of the securing portion on the second surface of the third band body portion when the pressing member is positioned in overlaying relation to the first puncture site of the patient's hand, or wrapping the third band body portion and the second band body portion around a portion of the patient's hand and mating the securing portion on the first surface of the second band body portion with the second branch portion of the securing portion on the second surface of the third band body portion when the pressing member is positioned in overlaying relation to the second puncture site of the patient's hand; and positioning the first band body portion between two fingers of the patient's hand and mating the securing portion on the first surface of the first band body portion with the securing portion on the second surface of the second band body portion.

DETAILED DESCRIPTION

Figure 1:
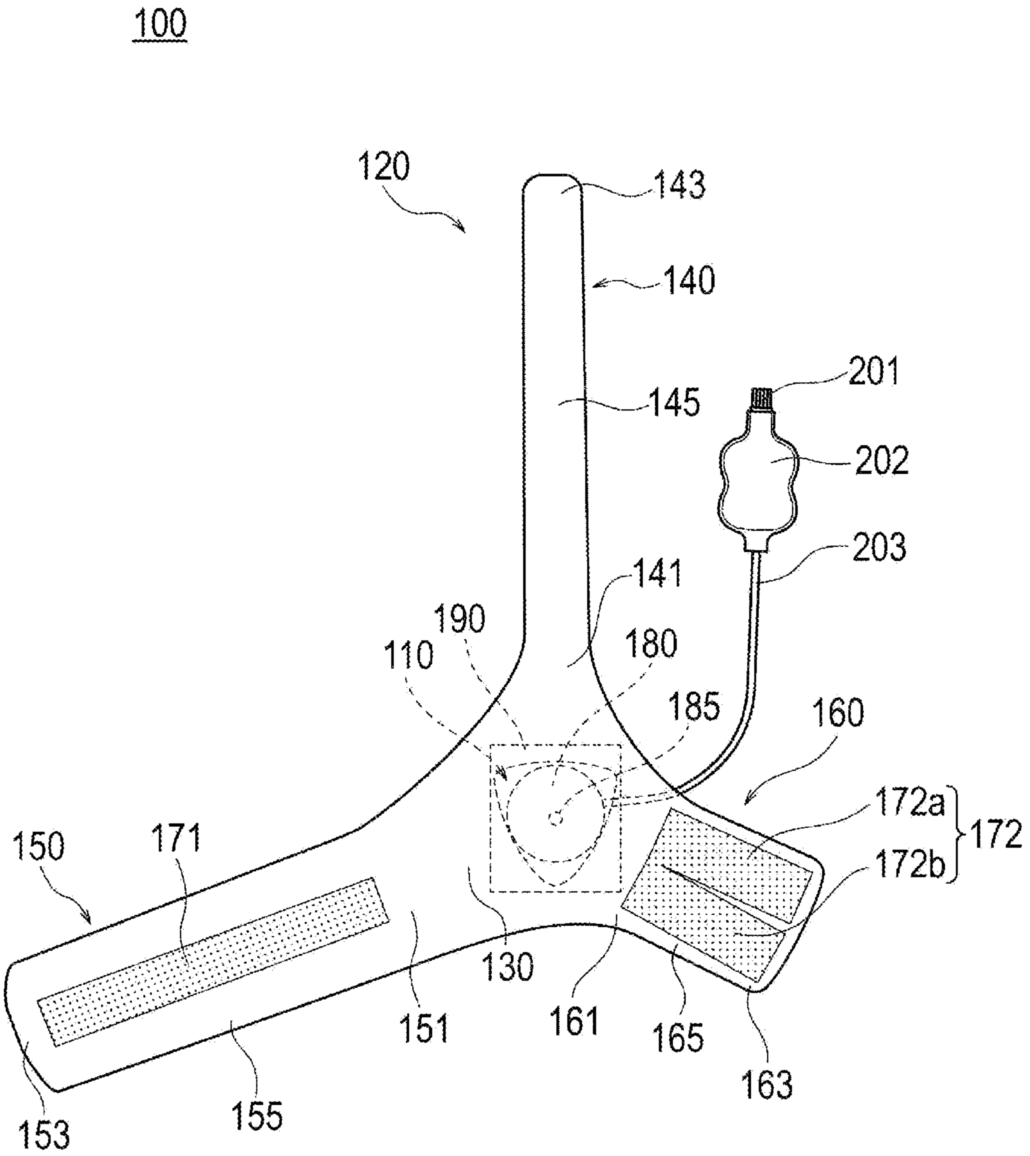
FIG. 1 is a plan view illustrating a hemostatic device according to Embodiment 1, viewed from an outer surface side of each band body portion.

Hereinafter, embodiments of the hemostatic device, representing examples of the new hemostatic device disclosed here, will be described with reference to the accompanying drawings. The following description does not limit the technical scope or the meaning of terms described in the claims. Further, dimensional ratios in the drawings are exaggerated for convenience of description and may differ from actual ratios.

Embodiment 1

FIGS. 1 to 9 are views illustrating a hemostatic device 100 according to the present embodiment, and FIGS. 10 to 17 are views illustrating usage examples and operational effects of the hemostatic device 100.

For example, as illustrated in FIGS. 10 and 13 to 17, the hemostatic device 100 can be used for hemostasis of a puncture site (for example, puncture sites p1, p2, p3, and p4 to be described later) formed in a hand H located on a far side (fingertip side) than a forearm A of a patient when a sheath tube of an introducer 300 indwelled in the puncture site is removed.

A specific position of the puncture site, which is a hemostasis target of the hemostatic device 100, is not particularly limited, and in the present embodiment, the following first puncture site p1, second puncture site p2, third puncture site p3, and fourth puncture site p4 are exemplified.

Figure 10:
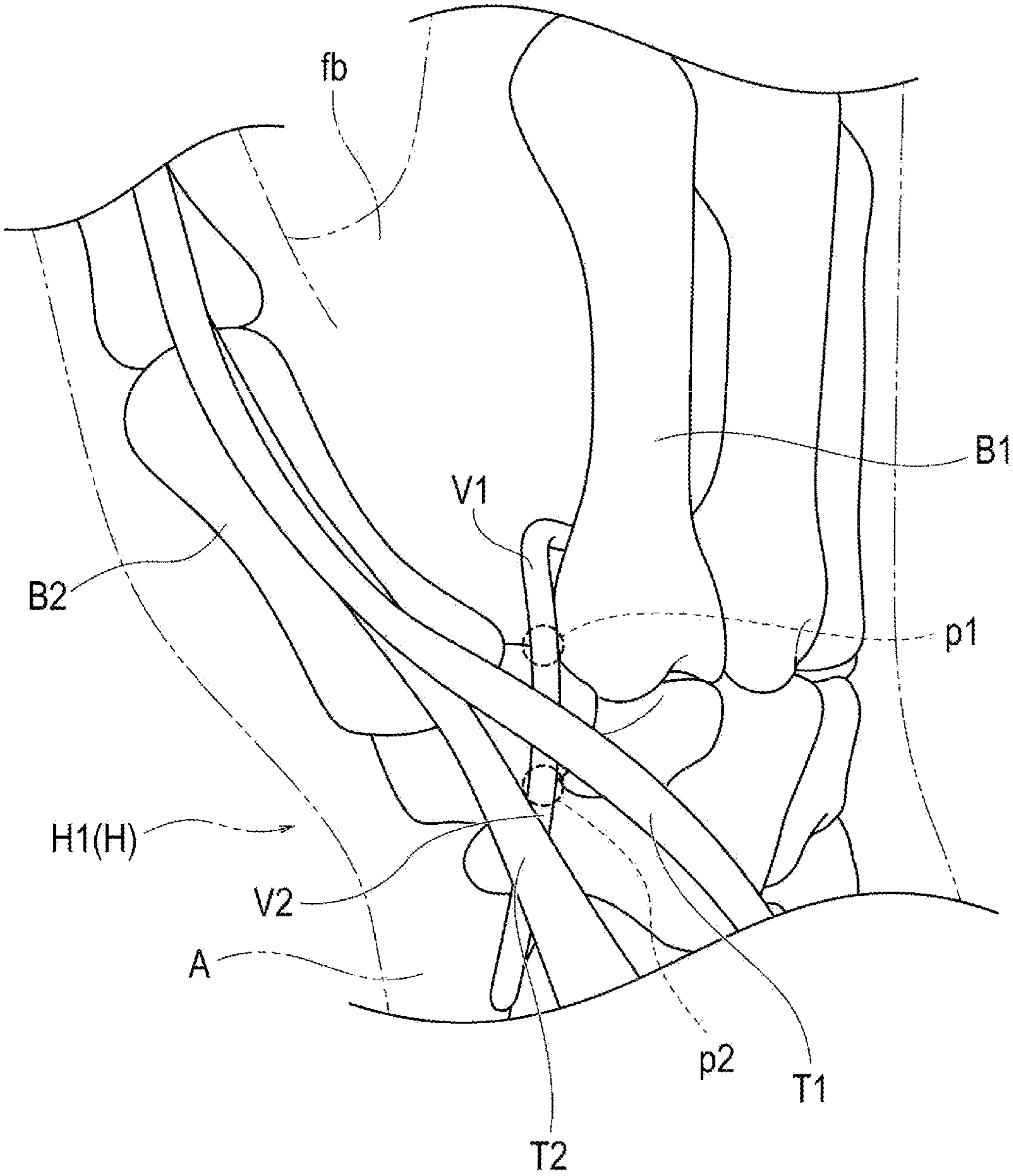
FIG. 10 is a view illustrating a hand (right hand) of a patient who uses the hemostatic device according to Embodiment 1.
Figure 13:
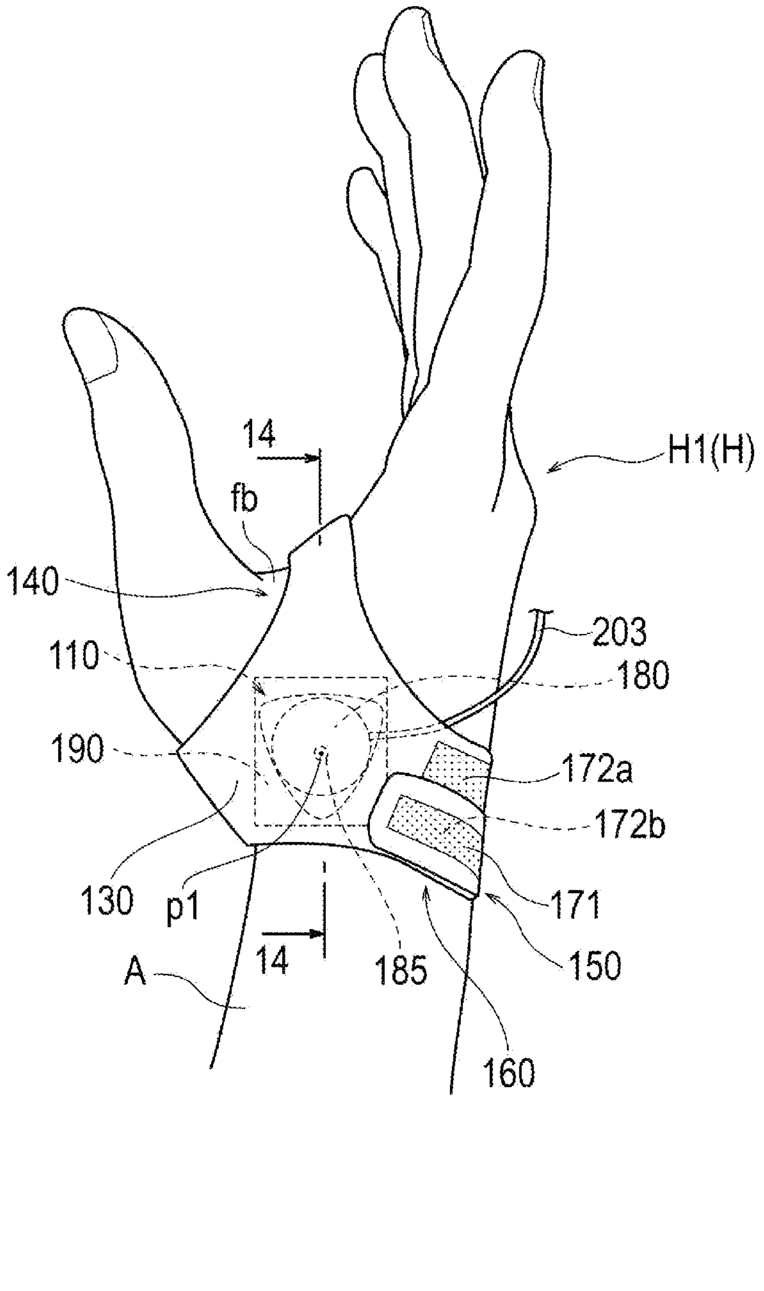
FIG. 13 is a view schematically illustrating the first usage example of the hemostatic device according to Embodiment 1.
Figure 14:
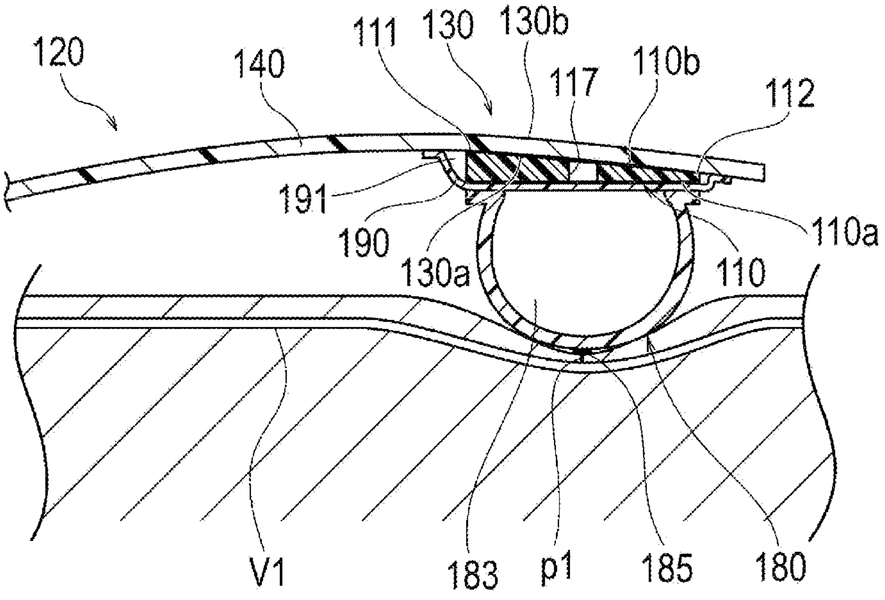
FIG. 14 is a partial cross-sectional view along the section line 14-14 illustrated in FIG. 13.

As illustrated in FIGS. 10, 13, and 14, the first puncture site p1 is a puncture site formed in a distal radial artery (hereinafter, also referred to as a "blood vessel V1") located on a far side of a snuff box of a palmar artery running on a dorsal side of a right hand H1 (hand H) located on the far side than the forearm A of the patient.

In addition, the first puncture site p1 is located at a predetermined position between a metacarpal bone B1 of an index finger and a metacarpal bone B2 of a thumb and avoiding the metacarpal bone B1 of the index finger and the metacarpal bone B2 of the thumb. The snuff box is a cavity in the hand located near the radius when the patient spreads the thumb of the hand H.

Figure 15:
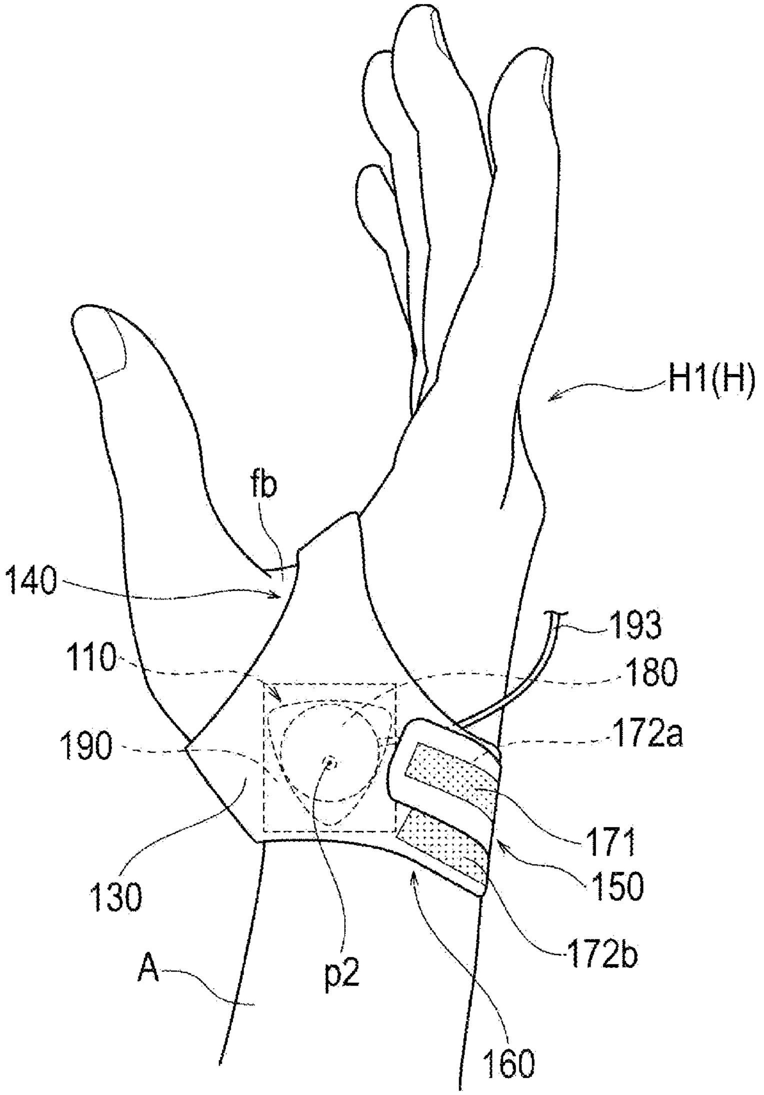
FIG. 15 is a view schematically illustrating a second usage example of the hemostatic device according to Embodiment 1.

As illustrated in FIGS. 10 and 15, the second puncture site p2 is a puncture site formed in an artery V2 located in the snuff box of the palmar artery running on the dorsal side of the right hand H1. The second puncture site p2 is located on the forearm A side of the patient than the first puncture site p1, and is located between an extensor pollicis longus muscle tendon T1 and an extensor pollicis brevis muscle tendon T2 located at the dorsal side of the right hand H1 of the patient. In addition, the second puncture site p2 is located at a predetermined position avoiding positions of the metacarpal bone B1 of the index finger and the metacarpal bone B2 of the thumb.

Figure 16:
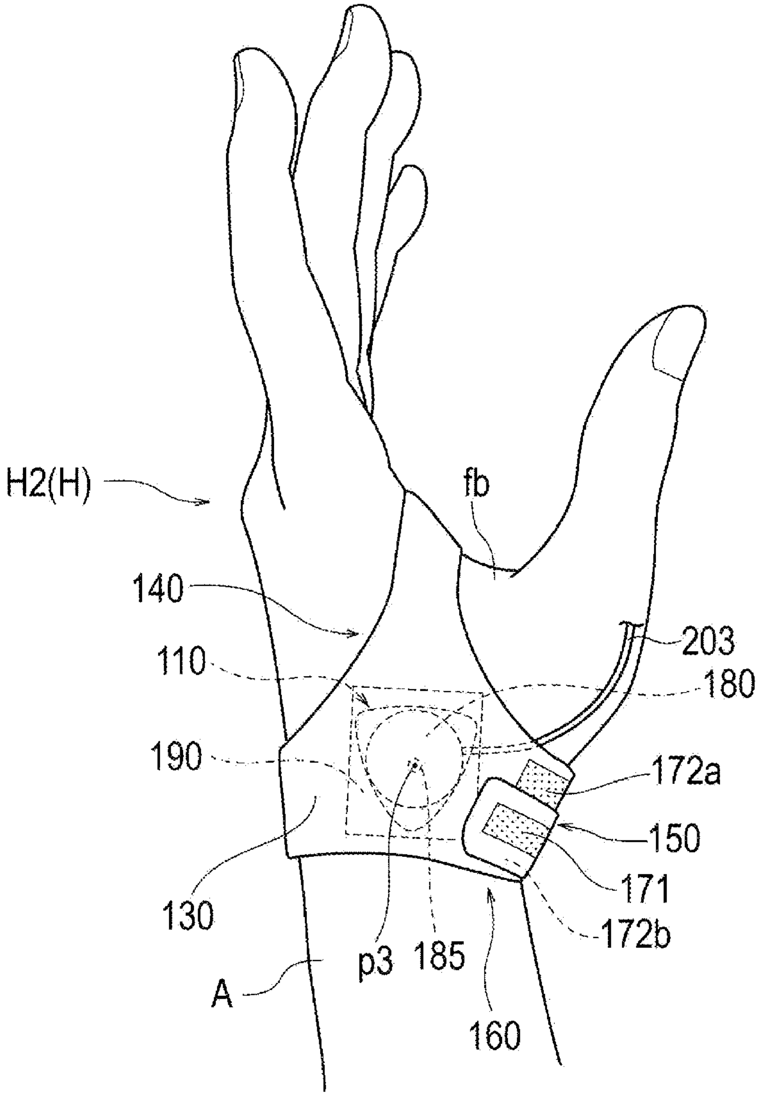
FIG. 16 is a view schematically illustrating a third usage example of the hemostatic device according to Embodiment 1.

As illustrated in FIG. 16, the third puncture site p3 is a puncture site formed on a left hand H2 (hand H) of the patient at a position corresponding to the first puncture site p1 exemplified by the right hand H1 of the patient.

Figure 17:
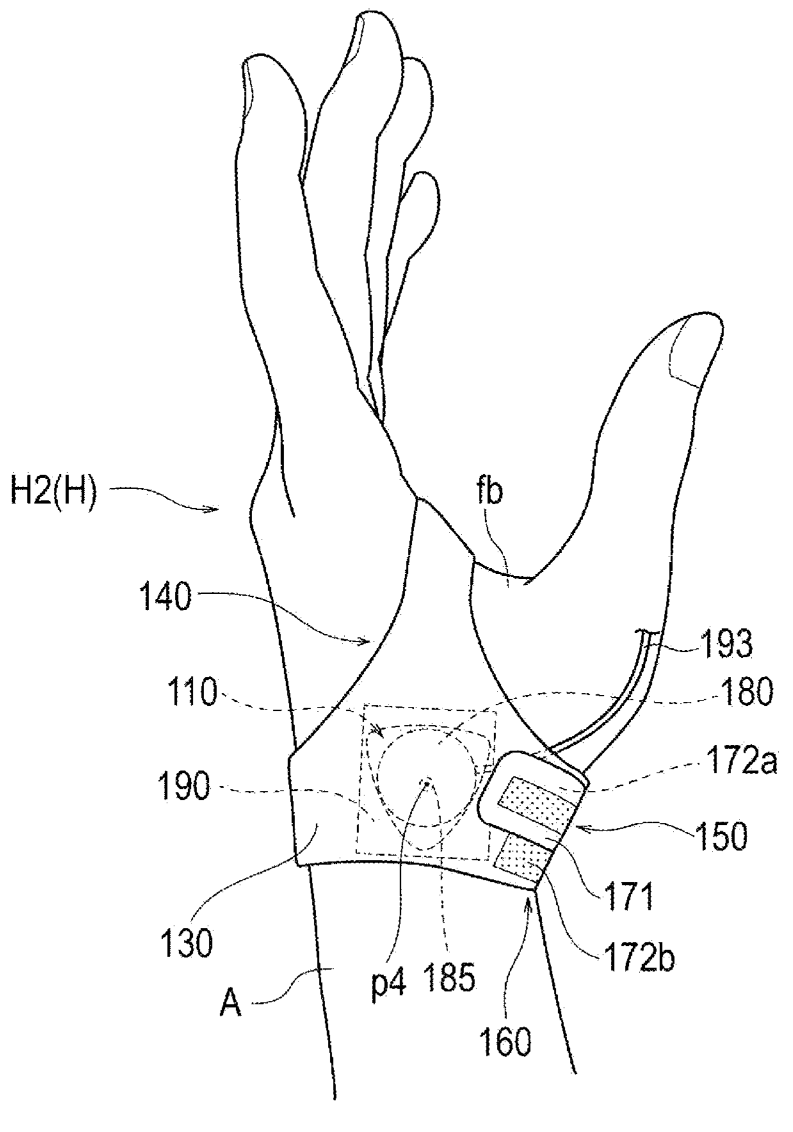
FIG. 17 is a view schematically illustrating a fourth usage example of the hemostatic device according to Embodiment 1.

As illustrated in FIG. 17, the fourth puncture site p4 is a puncture site formed on the left hand H2 (hand H) of the patient at a position corresponding to the second puncture site p2 exemplified by the right hand H1 of the patient.

In the description below, the first puncture site p1 formed on the right hand H1 of the patient is also simply referred to as a "first puncture site p1", and the second puncture site p2 formed on the right hand H1 of the patient is also simply referred to as a "second puncture site p2". The third puncture site p3 formed on the left hand H2 of the patient is also simply referred to as a "third puncture site p3", and the fourth puncture site p4 formed on the left hand H2 of the patient is also simply referred to as a "fourth puncture site p4".

Hereinafter, the hemostatic device 100 will be described in detail.

<Hemostatic Device>

Figure 5:
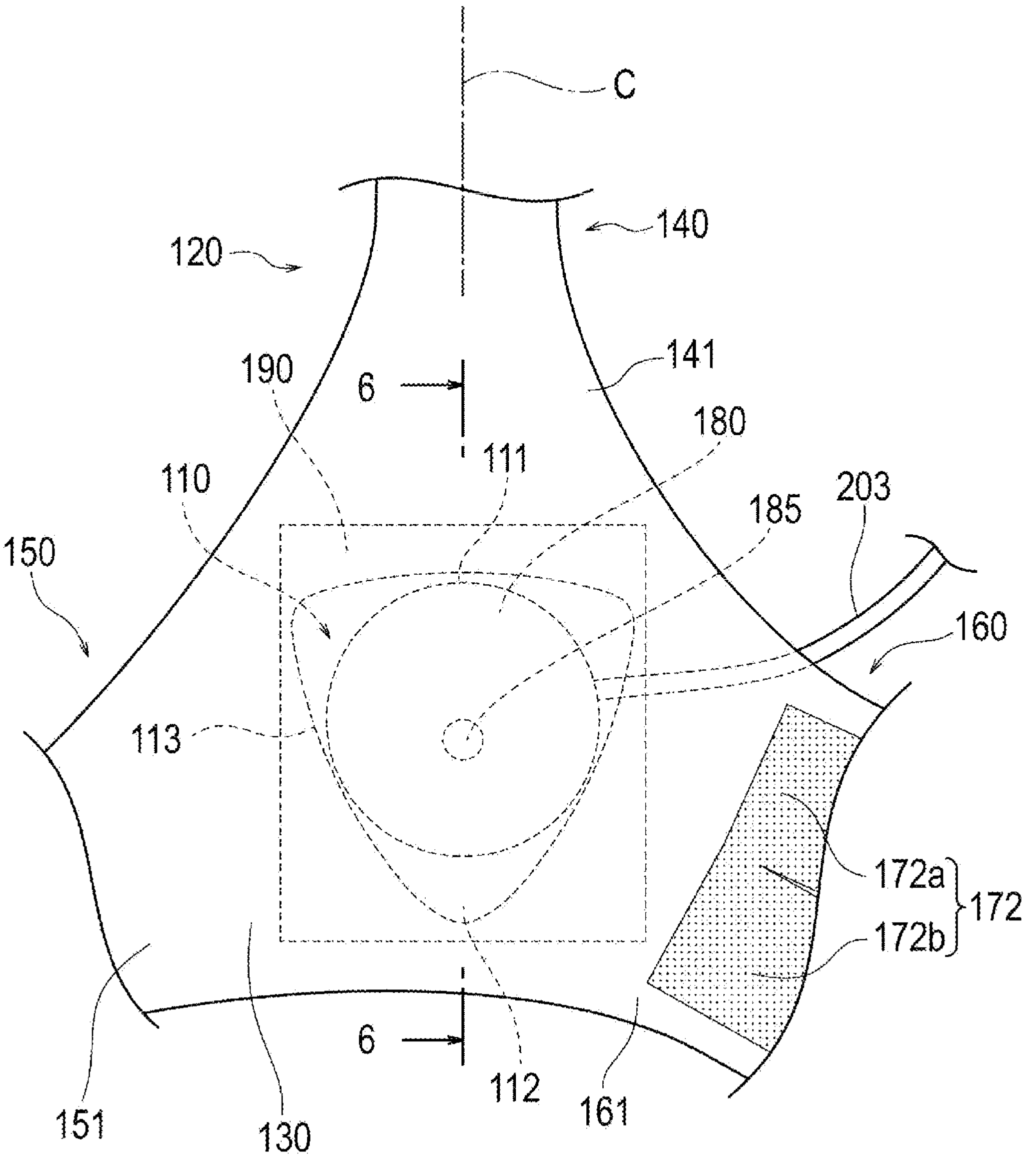
FIG. 5 is an enlarged plan view illustrating a part of the hemostatic device, viewed from the outer surface side of each band body portion.

In brief, as illustrated in FIGS. 1, 2, 13, and 14, the hemostatic device 100 includes: a support member 110 configured to cover the first puncture site p1; a securing member 120 configured to secure the support member 110 to the first puncture site p1; and a pressing member 180 connected to the support member 110 and configured to compress the first puncture site. The above phrase "connected to the support member 110" includes that the pressing member 180 is indirectly connected to the support member 110. For example, as illustrated in FIGS. 1, 5, and 6, the fact that the pressing member 180 (inflatable member 180) is connected to the support member 110 via a connection member 190 is included in the above phrase "connected to the support member 110".

<Pressing Member>

Figure 6:
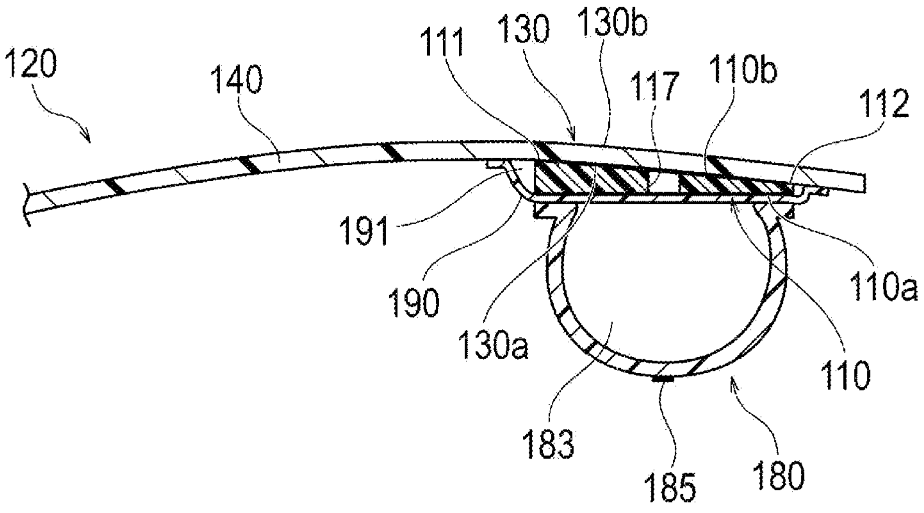
FIG. 6 is a partial cross-sectional view of the hemostatic device taken along the section line 6-6 illustrated in FIG. 5, and illustrating a state where a pressing member (inflatable member) is inflated.

For example, as illustrated in FIG. 6, the pressing member 180 can be constituted by an inflatable member such as a balloon including a lumen 183 into which a fluid such as air can flow. In the present embodiment, an example in which the pressing member 180 is constituted by the inflatable member will be described in the following description.

The inflatable member 180 is constituted by, for example, a single film-like or film-shaped member formed in a bag shape so as to include the lumen 183.

However, the inflatable member 180 may be formed by joining edge portions of two sheet-like or sheet-shaped film materials in a state where the lumen 183 is formed between the two sheet-like film materials formed in a substantially rectangular shape.

The inflatable member 180 is inflated by supply of a fluid such as air to the lumen 183, and contracts by discharging the fluid supplied to the lumen 183. FIG. 6 illustrates a cross-sectional view when the fluid is supplied to the inflatable member 180 and the inflatable member 180 is inflated.

The film materials for the inflatable member 180 can be, for example, a resin material having a predetermined thickness. A tube 203 (see FIGS. 1 and 2) to be described later is coupled to the lumen 183 of the inflatable member 180.

A material for the film-like member constituting the inflatable member 180 is not particularly limited, and examples thereof include polyvinyl chloride, polyolefin such as polyethylene, polypropylene, polybutadiene, or ethylene-vinyl acetate copolymer (EVA), polyester such as polyethylene terephthalate (PET) or polybutylene terephthalate (PBT), polyvinylidene chloride, silicone, polyurethane, various thermoplastic elastomers such as polyamide elastomer, polyurethane elastomer, and polyester elastomer, nylon, nylon elastomer, or any combination thereof (e.g., blended resin, polymer alloy, laminate, etc.).

As illustrated in FIG. 6, the inflatable member 180 is disposed on an inner surface 130*a* side of a covering portion 130 included in the securing member 120.

The inner surface 130*a* of the covering portion 130 is a surface disposed on a body surface side of the right hand H1 of the patient when the hemostatic device 100 is attached to the right hand H1 of the patient (see FIG. 14). In addition, an outer surface 130*b* of the covering portion 130 is a surface located on a side opposite to the inner surface 130*a*.

As illustrated in FIG. 6, the connection member 190 is disposed on the inner surface 130*a* of the covering portion 130. The inflatable member 180 can be connected to the support member 110 via the connection member 190. An outer peripheral edge of the inflatable member 180 can be connected to the connection member 190 by, for example, an adhesive or welding.

The connection member 190 is disposed so as to form a space 191 between the connection member 190 and the covering portion 130. The support member 110 is disposed in the space 191.

The connection member 190 can be constituted of, for example, a resin member. An outer peripheral edge of the connection member 190 can be connected to the covering portion 130 by, for example, the adhesive or the welding.

The inflatable member 180 has a circular shape in plan views illustrated in FIGS. 1 to 5. The shape of the inflatable member 180 in the plan views is not limited to a circular shape. In addition, a cross-sectional shape of the inflatable member 180 before and after inflating, a specific structure of the inflatable member 180, and the like are not particularly limited.

As illustrated in FIGS. 6, 13, and 14, a marker portion (marker) 185 for aligning the inflatable member 180 with the first puncture site p1 is disposed in the inflatable member 180.

As illustrated in FIG. 6, the marker portion 185 is disposed on an outer surface of the inflatable member 180. The marker portion 185 may be disposed on an inner surface of the inflatable member 180 facing the lumen 183.

In the marker portion 185, for example, the entire marker portion 185 can be formed of a colored rectangular marker. A specific shape, a color, a formation method, and a position formed in the inflatable member 180 of the marker portion 185 are not particularly limited. For example, the marker portion 185 may include a transparent central portion and a colored linear frame portion surrounding the central portion.

<Support Member>

As illustrated in FIGS. 5, 6, 7, 8, and 9, the support member 110 includes: an upper end portion 111 that is located on a distal side of the inflatable member 180 and forms an end portion of the support member 110; a lower end portion 112 that is located on a proximal side of the inflatable member 180 and forms an end portion on a side opposite to the upper end portion 111; and a side surface portion 113 that connects the upper end portion 111 and the lower end portion 112.

The "distal side of the inflatable member 180" means an end portion side (upper side in FIGS. 5 and 13) disposed on a fingertip side of the patient in the inflatable member 180 when the hemostatic device 100 is attached to the right hand H1 of the patient. In addition, the "proximal side of the inflatable member 180" means an end portion side (lower side in FIGS. 5 and 13) disposed on the forearm A side of the patient in the inflatable member 180 when the hemostatic device 100 is attached to the right hand H1 of the patient.

Figure 8:
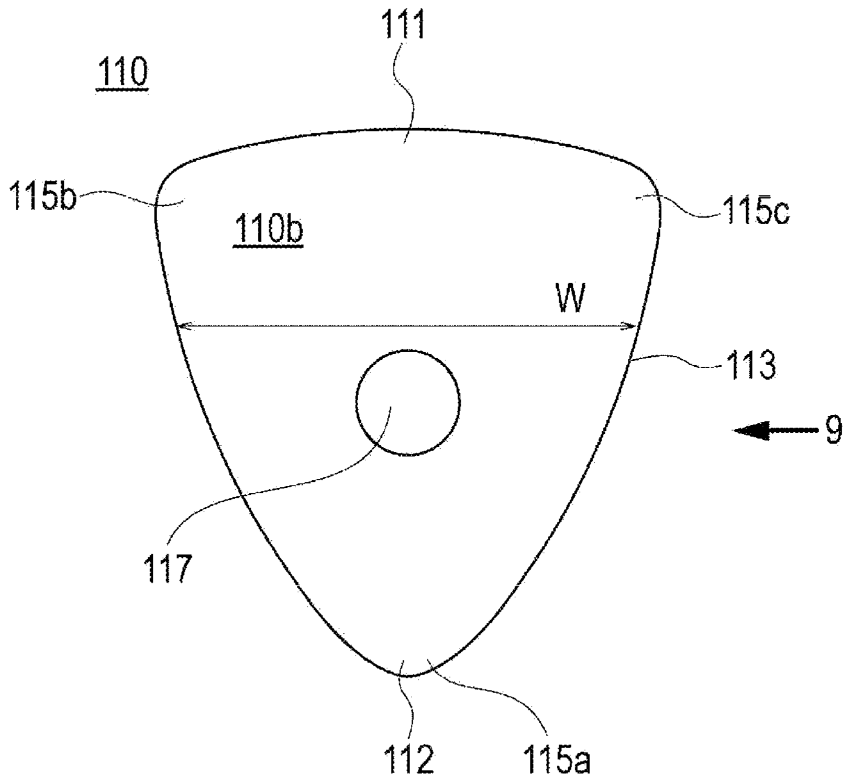
FIG. 8 is a plan view of the support member according to Embodiment 1.

As illustrated in FIG. 8, the support member 110 is configured such that a width W of the support member 110 becomes shorter from the upper end portion 111 toward the lower end portion 112.

Figure 9:
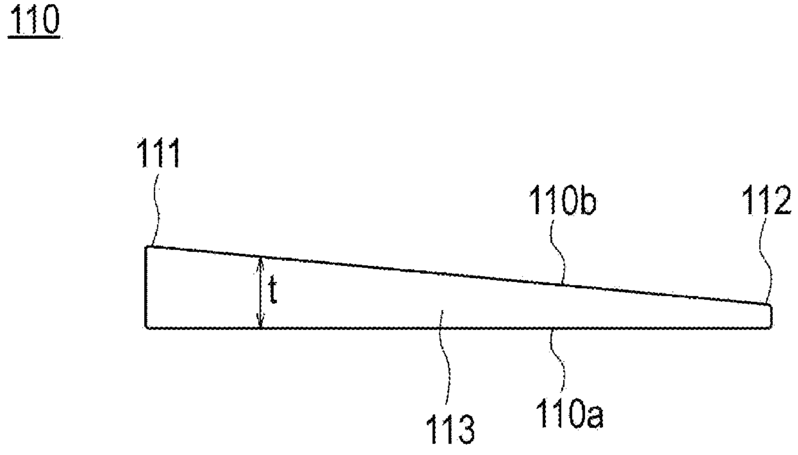
FIG. 9 is a side view of the support member according to Embodiment 1, viewed from a direction of an arrow 9 in FIG. 8.

In addition, as illustrated in FIG. 9, the support member 110 is configured such that a thickness of the side surface portion 113 becomes thinner from the upper end portion 111 toward the lower end portion 112. That is, in the cross-sectional view illustrated in FIG. 6 and a cross-sectional view illustrated in FIG. 9, an upper surface 110*b* of the support member 110 is inclined toward a lower surface 110*a* from the upper end portion 111 to the lower end portion 112.

The lower surface 110*a* of the support member 110 is a surface on which the inflatable member 180 is disposed, and the upper surface 110*b* is a surface on which the covering portion 130 is disposed.

As illustrated in FIG. 5, the support member 110 has a shape bilaterally symmetrical with respect to a long axis (axis along an extending direction) C of a first band body portion 140. Specifically, as illustrated in FIG. 8, the support member 110 has a substantially triangular planar shape. Corner portions 115*a*, 115*b*, and 115*c* located on an outer peripheral side surface of the support member 110 have a rounded shape.

Figure 7:
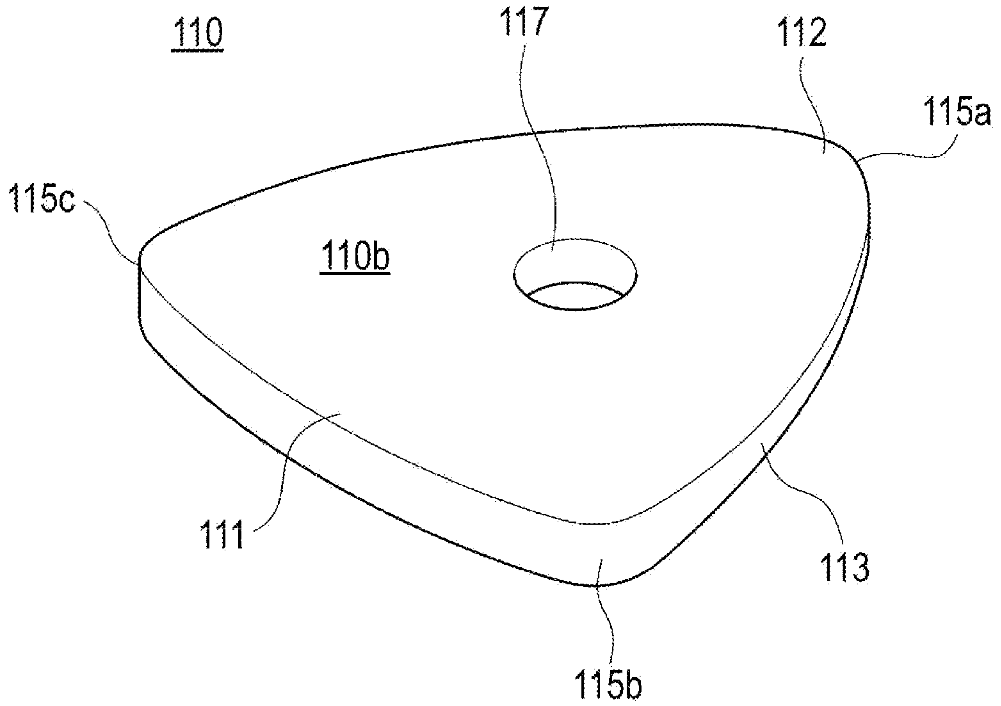
FIG. 7 is a perspective view of a support member according to Embodiment 1.

As illustrated in FIG. 7, the support member 110 has a hole 117 penetrating the support member 110 in a thickness direction. As illustrated in FIG. 6, the hole 117 can be disposed at a position overlapping the inflatable member 180. In the present embodiment, the hole 117 is disposed at a position overlapping the marker portion 185 disposed on the inflatable member 180.

Figure 11:
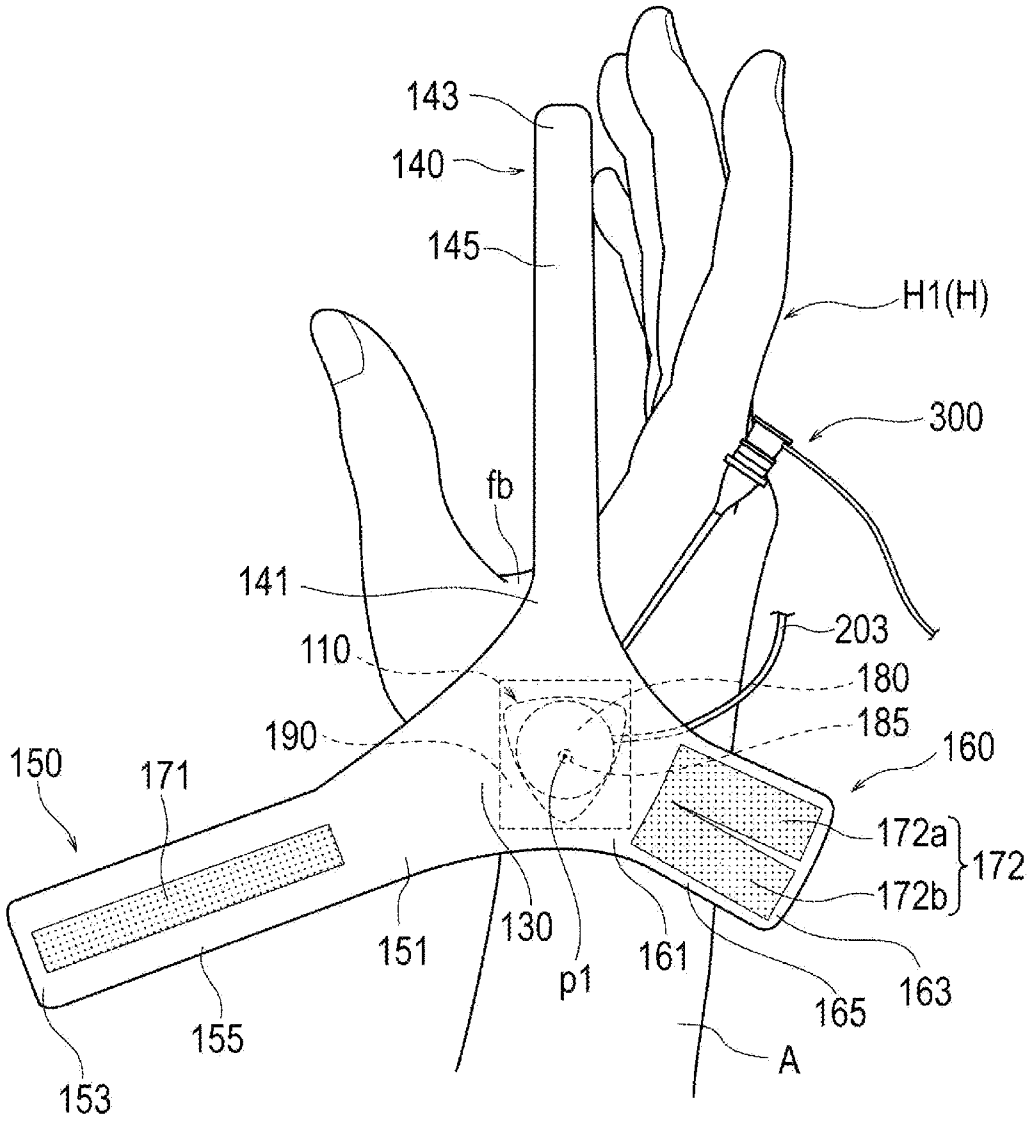
FIG. 11 is a view schematically illustrating a first usage example of the hemostatic device according to Embodiment 1.
Figure 12:
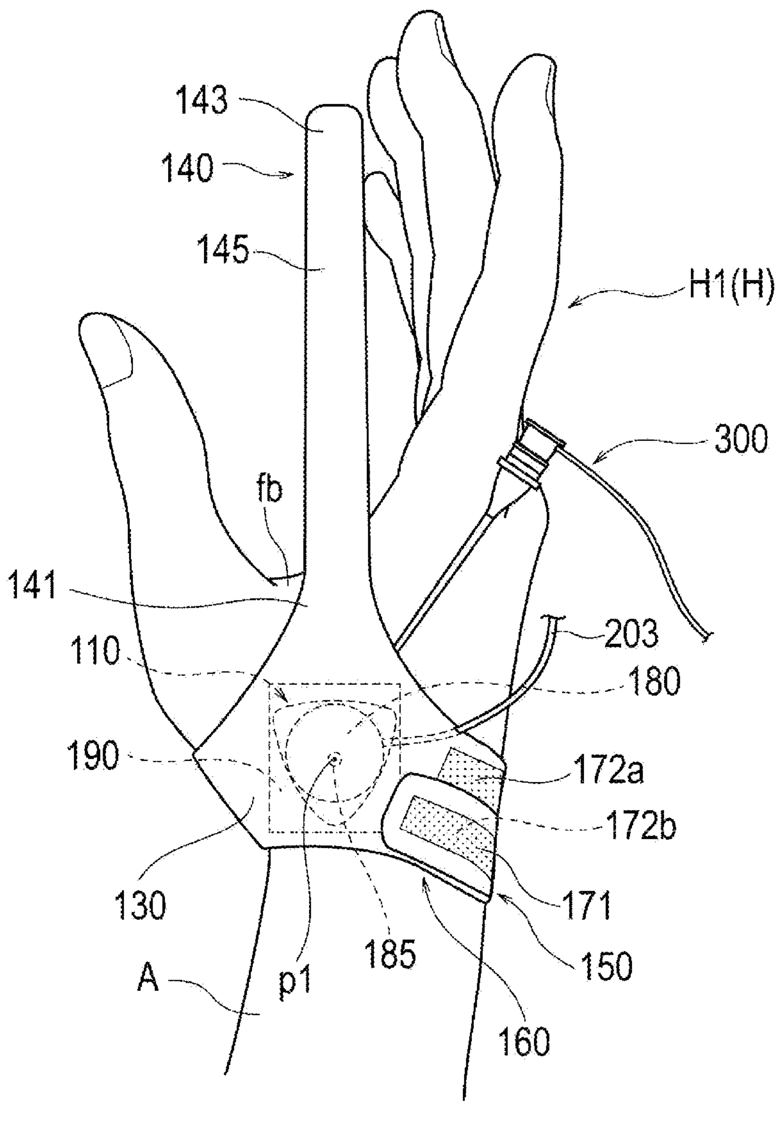
FIG. 12 is a view schematically illustrating the first usage example of the hemostatic device according to Embodiment 1.

In the hemostatic device 100, a portion of the inflatable member 180 where the marker portion 185 is provided, a portion of the connection member 190 overlapping the marker portion 185, and a portion of the covering portion 130 overlapping the marker portion 185 can be formed to be transparent. In a case where the members 130, 180, and 190 are configured in this way, when the hemostatic device 100 is attached to the right hand H1 of the patient as illustrated in FIGS. 11 to 13, an operator can easily visually confirm positions of the marker portion 185 disposed on the inflatable member 180 and/or the first puncture site p1 through the hole 117 of the support member 110 and transparent portions of the members 130, 180, and 190. The above term "transparent" includes colored transparent, colorless transparent, and translucent.

The support member 110 can be constituted of a member having rigidity higher than that of the inflatable member 180. With such a configuration, as illustrated in FIG. 14, when the inflatable member 180 applies a compressive force to the first puncture site p1, the support member 110 can press the inflatable member 180 against the right hand H1 of the patient. Accordingly, the inflatable member 180 can be prevented from lifting from the right hand H1 of the patient.

When the inflatable member 180 is constituted of the above-described materials, examples of the constituent materials of the support member 110 include an acrylic resin, polyvinyl chloride (in particular, hard polyvinyl chloride), polyolefin such as polyethylene, polypropylene, and polybutadiene, polystyrene, poly-(4-methylpentene-1), polycarbonate, ABS resin, polymethyl methacrylate (PMMA), polyacetal, polyacrylate, polyacrylonitrile, polyvinylidene sulfoxide, ionomer, acrylonitrile-butadiene-styrene copolymer, polyethylene terephthalate (PET), or the like.

<Securing Member>

As illustrated in FIGS. 1, 2, 3, 4, and 13, the securing member 120 includes the covering portion 130, the first band body portion 140, a second band body portion 150, and a third band body portion 160.

The covering portion 130 constitutes a main body portion to which the band body portions 140, 150, and 160 are connected. As illustrated in FIGS. 5 and 6, the support member 110, the inflatable member 180, and the connection member 190 are disposed in the covering portion 130.

In the securing member 120, the covering portion 130 and the band body portions 140, 150, and 160 may be integrally configured, or members configuring the band body portions 140, 150, and 160 may be connected to a member configuring the covering portion 130. In addition, the securing member 120 may not include the covering portion 130, and the band body portions 140, 150, and 160 may be directly connected to the support member 110.

The first band body portion 140 is configured to be disposed between fingers of the patient. The first band body portion 140 extends in a predetermined first direction.

Figure 2:
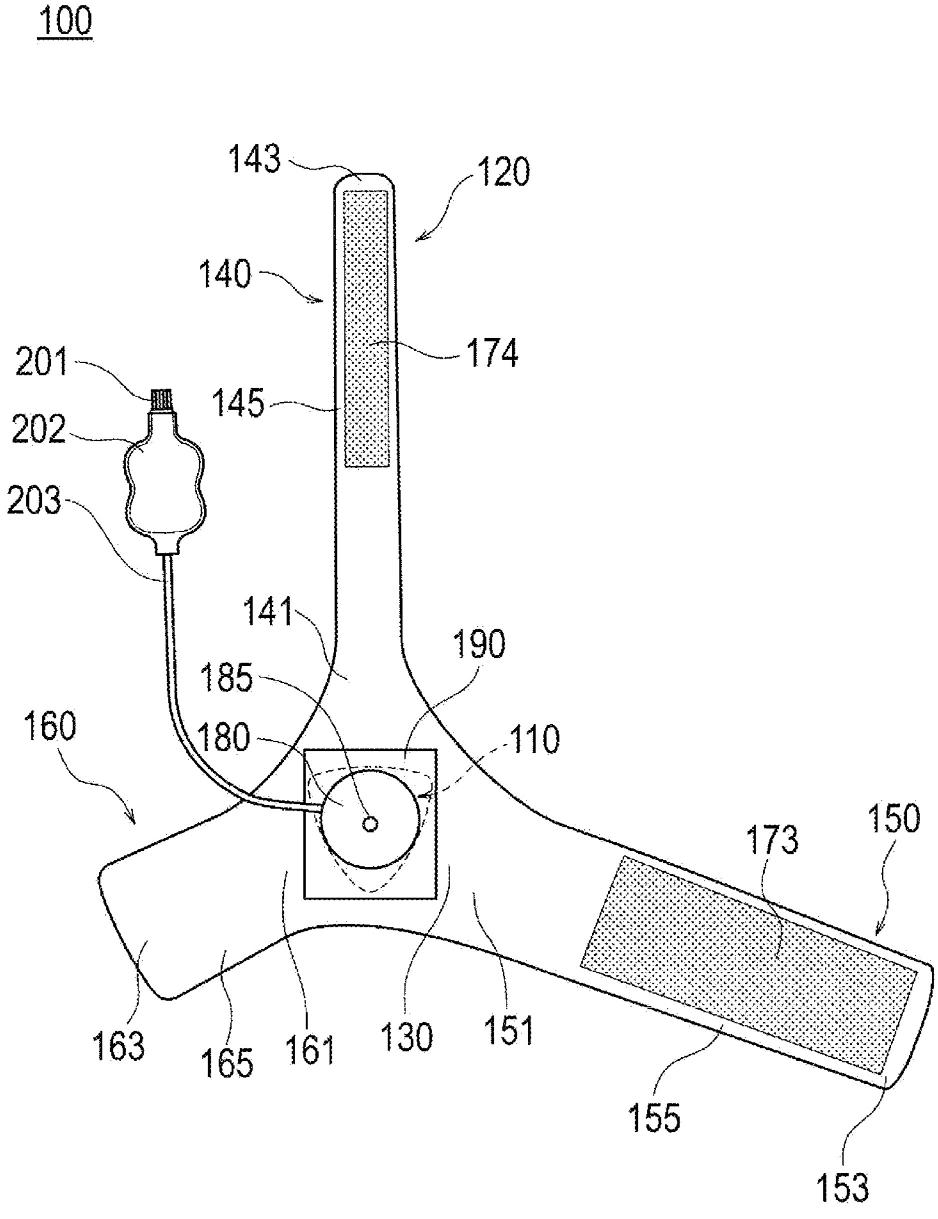
FIG. 2 is a plan view illustrating the hemostatic device according to Embodiment 1, viewed from an inner surface side of each band body portion.
Figure 3:
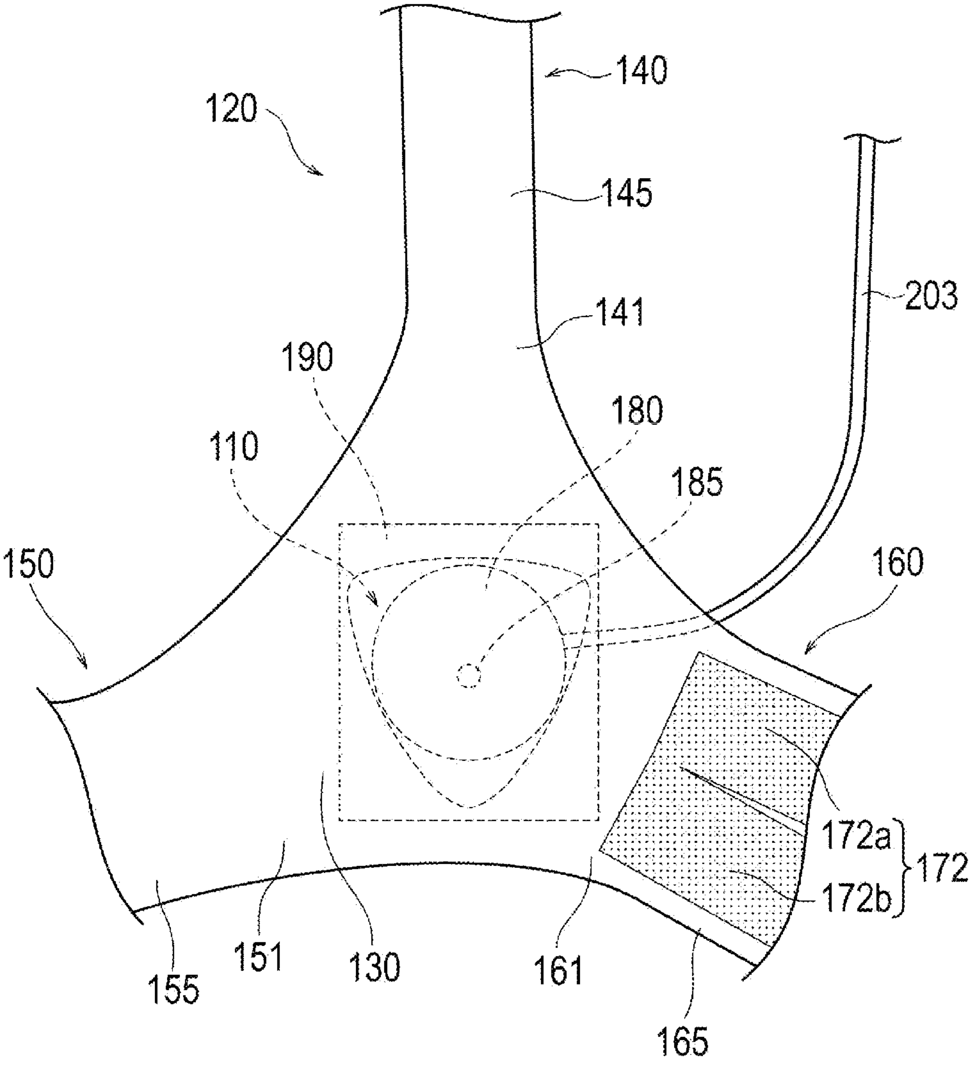
FIG. 3 is an enlarged view illustrating a part of the hemostatic device, viewed from the outer surface side of each band body portion.
Figure 4:
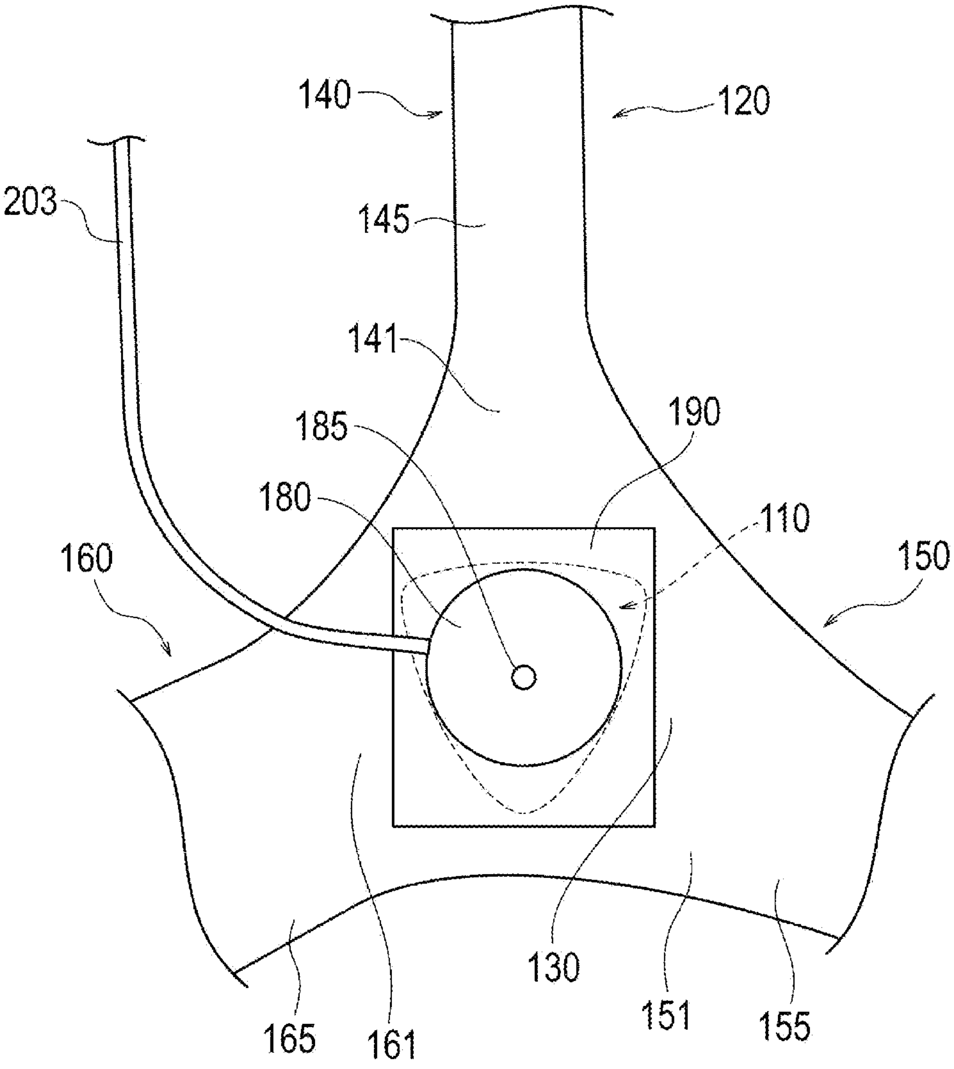
FIG. 4 is an enlarged view illustrating a part of the hemostatic device, viewed from the inner surface side of each band body portion.

As illustrated in FIGS. 1 and 2, the first band body portion 140 includes: one end portion 141 located on the support member 110 side; the other end portion 143 located on a side opposite to the one end portion 141; and a main body portion 145 extending between the one end portion 141 and the other end portion 143.

For example, as illustrated in FIG. 13, the first band body portion 140 can be disposed so as to be hooked on an inter-finger portion fb located between the thumb and the index finger of the right hand H1 of the patient in a state where the inflatable member 180 is disposed at the first puncture site p1.

The second band body portion 150 extends in a second direction different from the first direction that is an extending direction of the first band body portion 140. Specifically, as illustrated in FIG. 5, the second band body portion 150 extends from one side (left side in FIG. 5) of the side surface portion 113 of the support member 110.

As illustrated in FIGS. 1 and 2, the second band body portion 150 includes: one end portion 151 located on the support member 110 side; the other end portion 153 located on a side opposite to the one end portion 151; and a main body portion 155 extending between the one end portion 151 and the other end portion 153.

The third band body portion 160 extends in a third direction different from the first direction that is the extending direction of the first band body portion 140 and from the second direction that is an extending direction of the second band body portion 150. Specifically, as illustrated in FIG. 5, the third band body portion 160 extends from the other side (right side in FIG. 5) of the side surface portion 113 located on a side opposite to the second band body portion 150 with the support member 110 sandwiched or positioned therebetween.

As illustrated in FIGS. 1 and 2, the third band body portion 160 includes: one end portion 161 located on the support member 110 side; the other end portion 163 located on a side opposite to the one end portion 161; and a main body portion 165 extending between the one end portion 161 and the other end portion 163.

As illustrated in FIGS. 11, 12, and 13, when the hemostatic device 100 is attached to the right hand H1 of the patient, the second band body portion 150 and the third band body portion 160 can be disposed so as to be wrapped around an outer periphery of the right hand H1.

Constituent materials from which the band body portions 140, 150, and 160 may be fabricated are not particularly limited, and may include, for example, a vinyl chloride resin, a polyurethane resin, a polyester resin, or the like. In addition, a shape, a length, a thickness, and the like of each of the band body portions 140, 150, and 160 are not particularly limited.

As illustrated in FIGS. 1 and 2, the securing member 120 includes four securing sites, that is, a first securing site 171, a second securing site 172, a third securing site 173, and a fourth securing site 174 that allow the band body portions 140, 150, and 160 to be secured to the right hand H1 of the patient.

As illustrated in FIG. 1, the first securing site 171 is disposed on an outer surface of the main body portion 155 of the second band body portion 150. The second securing site 172 is disposed on an outer surface of the main body portion 165 of the third band body portion 160.

As illustrated in FIG. 2, the third securing site 173 is disposed on an inner surface of the main body portion 155 of the second band body portion 150. The fourth securing site 174 is disposed on an inner surface of the main body portion 145 of the first band body portion 140.

The first securing site 171 and the second securing site 172 are configured as a male side of a surface fastener. The third securing site 173 and the fourth securing site 174 are configured as a female side of the surface fastener. The surface fastener in the present specification is a fastener that is attachable and removable in terms of surface, and is, for example, Magic Tape (registered trademark) or Velcro (registered trademark).

The main body portion 155 of the second band body portion 150 and the main body portion 165 of the third band body portion 160 are configured to be attachable and removable via the third securing site 173 and the second securing site 172. In addition, the main body portion 145 of the first band body portion 140 and the main body portion 155 of the second band body portion 150 are configured to be attachable and removable via the first securing site 171 and the fourth securing site 174.

As illustrated in FIG. 1, in the second securing site 172 disposed in the main body portion 165 of the third band body portion 160, an end portion located on the other end portion 163 side of the third band body portion 160 is branched into a plurality of portions, that is, a first branch portion 172*a* and a second branch portion 172*b*. The branch portions 172*a* and 172*b* extend substantially linearly from a branch starting point formed on the one end portion 161 side of the third band body portion 160 toward the other end portion 163 side. In the illustrated embodiment shown in FIG. 1, the branch portions 172*a* and 172*b* are spaced apart from one another so that there is a space between the branch portions 172*a*, 172*b*.

Specific structures of the securing sites 171, 172, 173, and 174 are not limited as long as the support member 110 and the inflatable member 180 can be secured to the right hand H1 of the patient by connecting the band body portions 140, 150, and 160 to each other in a state where the hemostatic device 100 is disposed on the right hand H1 of the patient. For example, installation of some of the securing sites can be omitted, and positions where the securing sites are disposed on the band body portions 140, 150, and 160, and the like can be freely changed. In addition, when each of the securing sites 171, 172, 173, and 174 includes the surface fastener, the male side and the female side of the surface fastener may be interchanged. In addition, each of the securing sites 171, 172, 173, and 174 may include, for example, a snap, a button, a clip, a coupling mechanism including a frame portion in which a hole or a projection is formed and an engaged portion in which a hole engageable with the frame portion is formed, or the like.

<Injection Portion>

As illustrated in FIGS. 1 and 2, the hemostatic device 100 includes an injection portion 201 for injecting a fluid into the inflatable member 180.

The injection portion 201 includes a connector having an incorporated check valve (not illustrated). A syringe (not illustrated) can be connected to the injection portion 201.

A cushioning member 202 having an inflatable space is disposed between the injection portion 201 and the inflatable member 180. The cushioning member 202 includes a flexible bag-shaped member having a space formed inside. The cushioning member 202 may be provided with an arrow-shaped marker indicating a direction in which the syringe is inserted into the injection portion 201.

The injection portion 201 is connected to one end side of the cushioning member 202. A lumen of the injection portion 201 communicates with the space in the cushioning member 202. When the check valve incorporated in the injection portion 201 is closed, communication between the lumen of the injection portion 201 and the space of the cushioning member 202 is cut off.

A flexible tube 203 is connected to the other end side of the cushioning member 202. A lumen of the tube 203 communicates with the space of the cushioning member 202. In addition, the other end portion of the tube 203 which is opposite to one end portion connected to the cushioning member 202 is connected to the inflatable member 180. The lumen of the tube 203 communicates with the lumen 183 of the inflatable member 180.

To inflate the inflatable member 180, the operator inserts a distal tubular portion of a syringe (not illustrated) into the injection portion 201 to open the check valve. The operator injects air in the syringe into the lumen 183 of the inflatable member 180 by pushing a plunger of the syringe in a state where the check valve of the injection portion 201 is open.

When the air is injected into the lumen 183 of the inflatable member 180, the inflatable member 180 is inflated. When the inflatable member 180 is inflated, the cushioning member 202 communicating with the lumen 183 of the inflatable member 180 via the tube 203 expands. The operator can easily understand that the inflatable member 180 is inflated without leakage of air by visually confirming expansion of the cushioning member 202.

To contract the inflatable member 180, the operator inserts the distal tubular portion of the syringe into the injection portion 201 and pulls the plunger of the syringe. By performing the above operation, the operator can discharge the air in the lumen 183 of the inflatable member 180 to the syringe.

The injection portion 201, the cushioning member 202, and the tube 203 may be prepared and provided in a state of being coupled to the inflatable member 180, or may be prepared and provided in a state of being separated from the inflatable member 180.

<Usage Examples of Hemostatic Device>

Next, a first usage example of the hemostatic device 100 will be described with reference to FIGS. 10 to 14.

In the first usage example, a use procedure of the hemostatic device 100 when the hemostasis is performed on the first puncture site p1 formed on the right hand H1 of the patient illustrated in FIG. 10 will be described.

FIG. 11 illustrates a state after performing various procedures performed using the sheath tube of the introducer 300 inserted into the first puncture site p1.

When the hemostatic device 100 is attached to the right hand H1 of the patient, as illustrated in FIG. 11, the operator disposes the inflatable member 180 and the support member 110 so as to overlap the first puncture site p1. At this time, the operator can appropriately position the inflatable member 180 and the support member 110 at the first puncture site p1 by disposing the marker portion 185 at the first puncture site p1 while visually confirming a position of the marker portion 185 disposed on the inflatable member 180 through the hole portion 117 (see FIG. 7) formed in the support member 110.

When the hemostatic device 100 is attached to the right hand H1 of the patient, the operator disposes the support member 110 so that the support member 110 overlaps the metacarpal bone B1 of the index finger and the metacarpal bone B2 of the thumb. As illustrated in FIG. 10, a distance between the metacarpal bone B1 of the index finger and the metacarpal bone B2 of the thumb gradually decreases from the fingertip side toward the forearm A side. As described above, the width W of the support member 110 becomes shorter from the upper end portion 111 toward the lower end portion 112 (see FIG. 8). Therefore, the operator can dispose the support member 110 along the metacarpal bone B1 of the index finger and the metacarpal bone B2 of the thumb. The operator can prevent a gap from being generated between the inflatable member 180 and the right hand H1 by disposing the support member 110 along the metacarpal bone B1 of the index finger and the metacarpal bone B2 of the thumb.

As illustrated in FIG. 12, the operator wraps the second band body portion 150 and the third band body portion 160 along the outer periphery of the right hand H1 of the patient. The operator can connect the second band body portion 150 and the third band body portion 160 via the securing sites 172 and 173 by bringing the third securing site 173 (see FIG. 2) disposed on an inner surface of the second band body portion 150 into contact with the second securing site 172 (see FIG. 1) disposed on an outer surface of the third band body portion 160. The operator can firmly wrap the band body portions 150 and 160 along the outer periphery of the right hand H1 by connecting the band body portions 150 and 160 to each other in a state where the support member 110 overlaps the metacarpal bone B1 of the index finger and the metacarpal bone B2 of the thumb.

When the hemostasis is performed on the first puncture site p1, the operator can connect the third securing site 173 disposed on the inner surface of the second band body portion 150 to the second branch portion 172*b* of the second securing site 172. The first puncture site p1 is located on a fingertip side of the right hand H1 of the patient than the second puncture site p2 (see FIG. 10). Therefore, when the hemostasis is performed on the first puncture site p1, the operator connects the second band body portion 150 and the third band body portion 160 via the second branch portion 172*b* located on the forearm A side of the right hand H1 of the patient than the first branch portion 172*a*, thereby narrowing a range in which the band body portions 150 and 160 restrain the right hand H1 of the patient.

In addition, the second securing site 172 is disposed in the main body portion 165 of the third band body portion 160. Therefore, a part of the main body portion 165 is between the second securing site 172 and the one end portion 161 of the third band body portion 160. When the operator wraps the third band body portion 160 around the right hand H1 of the patient, by pulling the main body portion 165 using the one end portion 161 of the third band body portion 160 as a base point, the first branch portion 172*a* not used for connecting the second band body portion 150 and the third band body portion 160 can be prevented from being lifted from the right hand H1 of the patient.

For the above reasons, when the operator connects the second band body portion 150 and the third band body portion 160 via the second branch portion 172*b*, the lifting of the first branch portion 172*a* can be prevented (see FIGS. 15 and 17).

Figure 18:
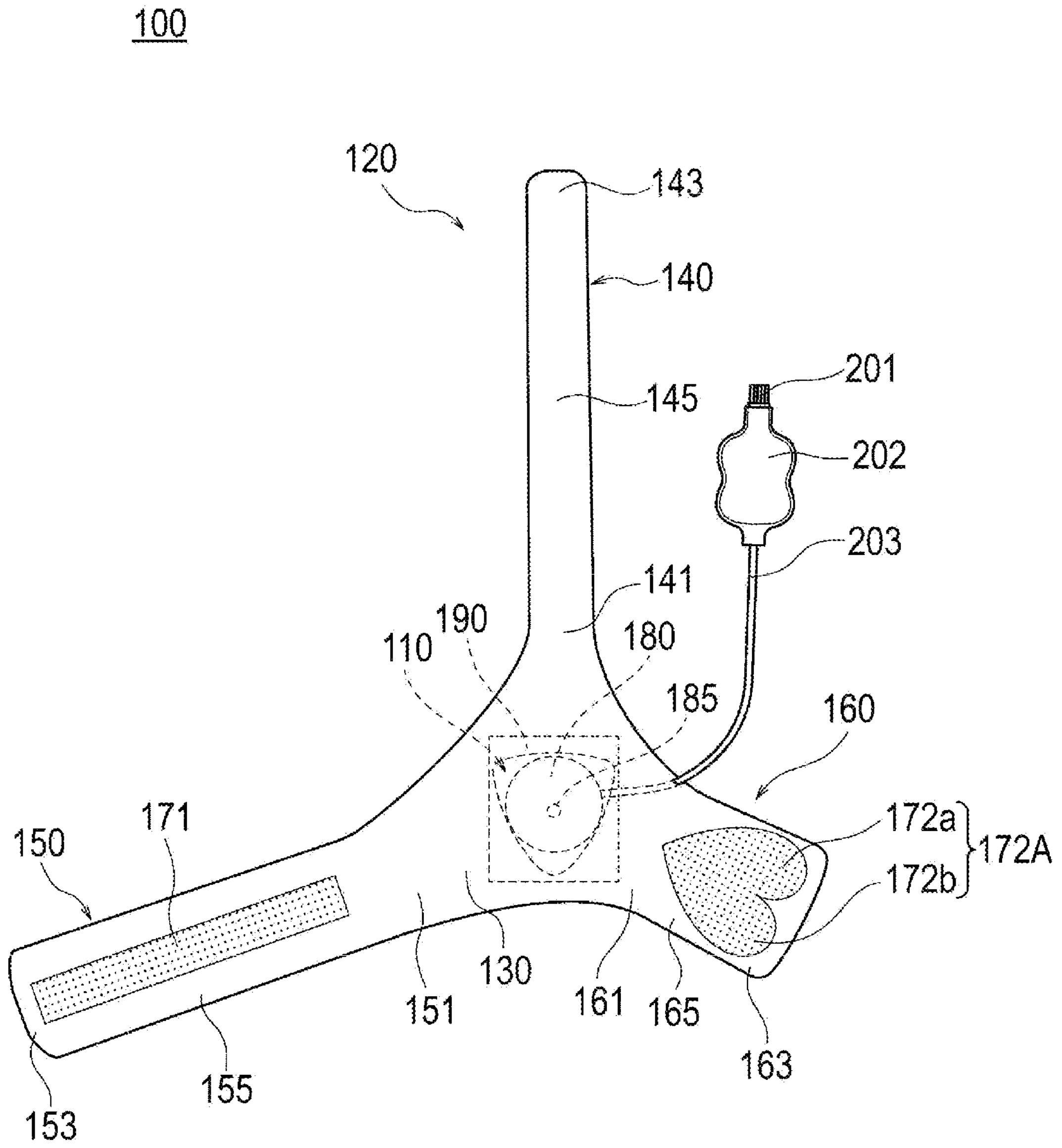
FIG. 18 is a plan view illustrating a hemostatic device according to a modification of Embodiment 1, viewed from the outer surface side of each band body portion.

It is also possible to adopt a configuration in which the third band body portion 160 itself is divided into a plurality of portions, and each of the portions of the third band body portion 160 is provided with a separate second securing site 172 (see FIG. 19), as an alternative to providing a second securing site 172 that is split into the first branch portion 172*a* and the second branch portion 172*b* as shown in FIGS. 1 and 18. If the third band body portion 160 is divided at the one end portion 161 located on the covering portion 130 side, when the operator wraps the third band body portion 160 around the right hand H1 of the patient, an entire range (side) of the covering portion 130 to which the third band body portion 160 is connected cannot be pressed down by the second band body portion 150. Therefore, the force holding the covering portion 130 and the third band body portion 160 against the right hand H1 decreases. In addition, when the third band body portion 160 is divided, a portion of the third band body portion 160 that is not connected to the second band body portion 150 while the hemostatic device 100 is being used hangs down from the hemostatic device 100. Therefore, the third band body portion 160 interferes with the attachment of the hemostatic device 100. In addition, when the third band body portion 160 is divided, a width of the third band body portion 160 has to be increased. Accordingly, it is difficult to form the second band body portion 150 and the third band body portion 160 to have substantially the same width. As a result, when the hemostatic device 100 is attached to the right hand H1 of the patient, it is difficult to apply a force uniformly to a position where the second band body portion 150 is wrapped and to a position where the third band body portion 160 is wrapped. The embodiments shown in FIGS. 1 and 18 may thus be preferable to the FIG. 19 embodiment.

As illustrated in FIG. 13, the operator passes the first band body portion 140 through the inter-finger portion fb located between the thumb and the index finger of the right hand H1 of the patient, and disposes a part of the first band body portion 140 on the palm side of the right hand H1 of the patient. At this time, the operator can connect the first band body portion 140 and the second band body portion 150 via the securing sites 172 and 174 by bringing the fourth securing site 174 (see FIG. 2) disposed on an inner surface of the first band body portion 140 into contact with the first securing site 171 (see FIG. 1) disposed on an outer surface of the second band body portion 150.

The support member 110 has a substantially triangular shape having three sides. The hemostatic device 100 includes three band body portions 140, 150, and 160 disposed to extend from each side of the support member 110. Therefore, the hemostatic device 100 can secure the support member 110 to the right hand H1 of the patient in a state in which a uniform force is applied to each side of the support member 110 by connecting the band body portions 140, 150, and 160 to each other.

In addition, the support member 110 has a shape bilaterally symmetrical with respect to the long axis C of the first band body portion 140. Therefore, the hemostatic device 100 can uniformly apply a force along a left-right direction to the support member 110 by wrapping the band body portions 150 and 160 extending in the left-right direction based on the first band body portion 140 around the right hand H1 of the patient. Accordingly, the hemostatic device 100 can prevent positional deviation of the support member 110 in a state where the support member 110 is disposed on the right hand H1 of the patient.

The operator inflates the inflatable member 180 by injecting air into the inflatable member 180 in a state where the syringe is connected to the injection portion 201. In the hemostatic device 100, as illustrated in FIG. 14, when the inflatable member 180 is inflated, the inflatable member 180 applies a compressive force to the first puncture site p1.

When the inflatable member 180 is inflated in a state where the hemostatic device 100 is attached to the right hand H1 of the patient, the support member 110 presses the inflatable member 180 against the right hand H1 of the patient. Accordingly, the hemostatic device 100 can prevent the inflatable member 180 from lifting from the right hand H1 of the patient.

When performing hemostasis using the hemostatic device 100, the operator can more strongly tighten the first band body portion 140 disposed in the inter-finger portion fb so as to increase a securing force of the support member 110 with respect to the right hand H1 of the patient. By tightening the first band body portion 140 as described above, the operator can firmly secure the support member 110 to the right hand H1 of the patient even when the support member 110 is disposed in an unstable state on the right hand H1 of the patient. When the first band body portion 140 is strongly tightened as described above, pain may occur in the patient. Therefore, when the first band body portion 140 cannot be strongly tightened due to pain or the like of the patient, the hemostatic device 100 may be disposed such that the lower surface 110*a* of the support member 110 is inclined with respect to the body surface of the right hand H1 of the patient.

To solve the above problem, the hemostatic device 100 is configured such that the thickness of the side surface portion 113 of the support member 110 becomes thinner from the upper end portion 111 toward the lower end portion 112. In addition, the first band body portion 140 configured to be disposed in the inter-finger portion fb located between the fingers of the patient extends from the upper end portion 111 side of the support member 110, and is configured to press the upper end portion 111 side of the support member 110 against the right hand H1 of the patient. Therefore, when the inflatable member 180 starts inflating in the state where the hemostatic device 100 is attached to the right hand H1 of the patient, the inflatable member 180 applies a force to the upper end portion 111 of the support member 110. The upper end portion 111 side of the support member 110 is lifted by the force applied by the inflatable member 180. Accordingly, as illustrated in FIG. 14, the support member 110 is disposed such that the lower surface 110*a* of the support member 110 is substantially parallel to the body surface of the right hand H1 of the patient. Therefore, when the inflatable member 180 is inflated, the hemostatic device 100 can apply a compressive force to the first puncture site p1 in a vertical direction.

The corner portions 115*a*, 115*b*, and 115*c* of the support member 110 have the rounded shape (see FIG. 8). Therefore, when the inflatable member 180 is inflated to apply a compressive force to the puncture site p1, the hemostatic device 100 can prevent the corner portions 115*a*, 115*b*, and 115*c* of the support member 110 from biting into the right hand H1 of the patient.

According to the above procedures, the operator can perform the hemostasis on the first puncture site p1 formed in the right hand H1 of the patient using the hemostatic device 100.

Next, a second usage example to a fourth usage example of the hemostatic device 100 will be described with reference to FIGS. 15 to 17. In the descriptions of the second usage example to the fourth usage example, details and aspects of the hemostatic device described above and as a part of the first usage example will not be repeated.

FIG. 15 illustrates the second usage example of the hemostatic device 100. The second usage example is a method of performing hemostasis on the second puncture site p2 (see FIG. 10) using the hemostatic device 100. In the second usage example, the operator can connect the second band body portion 150 and the third band body portion 160 via the securing sites 172 and 173 by bringing the third securing site 173 (see FIG. 2) disposed on the inner surface of the second band body portion 150 into contact with the first branch portion 172*a* of the second securing site 172 (see FIG. 1) disposed on the outer surface of the third band body portion 160.

When the hemostasis is performed on the second puncture site p2, the operator connects the second band body portion 150 and the third band body portion 160 via the first branch portion 172*a* located on the fingertip side of the patient than the second branch portion 172*b*, thereby narrowing the range in which the right hand H1 of the patient is restrained by the band body portions 150 and 160.

FIG. 16 illustrates the third usage example of the hemostatic device 100.

The third usage example is a method of performing hemostasis on the third puncture site p3 formed on the left hand H2 of the patient using the hemostatic device 100. In the third usage example, the operator can connect the second band body portion 150 and the third band body portion 160 via the securing sites 172 and 173 by bringing the third securing site 173 (see FIG. 2) disposed on the inner surface of the second band body portion 150 into contact with the second branch portion 172*b* of the second securing site 172 (see FIG. 1) disposed on the outer surface of the third band body portion 160, as in the case of performing the hemostasis on the first puncture site p1.

When the hemostasis is performed on the third puncture site p3, the operator connects the second band body portion 150 and the third band body portion 160 via the second branch portion 172*b* located on the forearm A side of the left hand H2 of the patient than the first branch portion 172*a*, thereby narrowing a range in which the left hand H2 of the patient is restrained by the band body portions 150 and 160.

FIG. 17 illustrates the fourth usage example of the hemostatic device 100.

The fourth usage example is a method of performing hemostasis on the fourth puncture site p4 formed on the left hand H2 of the patient using the hemostatic device 100. In the fourth usage example, the operator can connect the second band body portion 150 and the third band body portion 160 via the securing sites 172 and 173 by bringing the third securing site 173 (see FIG. 2) disposed on the inner surface of the second band body portion 150 into contact with the first branch portion 172*a* of the second securing site 172 (see FIG. 1) disposed on the outer surface of the third band body portion 160, as in the case of performing the hemostasis on the second puncture site p2.

When the hemostasis is performed on the fourth puncture site p4, the operator connects the second band body portion 150 and the third band body portion 160 via the first branch portion 172*a* located on a fingertip side of the left hand H2 of the patient than the second branch portion 172*b*, thereby narrowing the range in which the left hand H2 of the patient is restrained by the band body portions 150 and 160.

As described above, the hemostatic device 100 according to present embodiment includes the support member 110 configured to cover the first puncture site p1, the securing member 120 configured to secure the support member 110 to the first puncture site p1, and the inflatable member 180 connected to the support member 110 and configured to compress the first puncture site p1. The support member 110 includes: the upper end portion 111 that is located on the distal side of the inflatable member 180 and forms the end portion of the support member 110; the lower end portion 112 that is located on the proximal side of the inflatable member 180 and forms the end portion of the side opposite to the upper end portion 111; and the side surface portion 113 that connects the upper end portion 111 and the lower end portion 112, and the support member 110 has rigidity higher than that of the inflatable member 180. The securing member 120 includes: the first band body portion 140 configured to be disposed between the fingers of the patient and extending in the first direction; and the second band body portion 150 extending in the second direction different from the first direction. The support member 110 is configured such that the width W of the support member 110 becomes shorter from the upper end portion 111 toward the lower end portion 112, and the thickness of the side surface portion 113 becomes thinner from the upper end portion 111 toward the lower end portion 112. The first band body portion 140 extends in the first direction from the upper end portion 111 side, and the second band body portion 150 extends in the second direction from the side surface portion 113 side.

The hemostatic device 100 configured as described above includes the support member 110 having rigidity higher than that of the inflatable member 180. The support member 110 is disposed so as to cover the first puncture site p1 together with the inflatable member 180 when the hemostasis is performed on the first puncture site p1 formed at a predetermined position avoiding the metacarpal bone B1 of the index finger of the right hand H1 of the patient and the metacarpal bone B2 of the thumb of the right hand H1 of the patient. The support member 110 can prevent the inflatable member 180 from being lifted from the right hand H1 of the patient by pressing the inflatable member 180 against the right hand H1 of the patient. In addition, the width W of the support member 110 becomes shorter from the upper end portion 111 toward the lower end portion 112. Therefore, when the support member 110 is disposed on the right hand H1 of the patient, the support member 110 can be disposed along the metacarpal bone B1 of the index finger and the metacarpal bone B2 of the thumb. Therefore, the second band body portion 150 can be firmly wrapped along the outer periphery of the right hand H1 of the patient. In addition, in the support member 110, the thickness of the side surface portion 113 becomes thinner from the upper end portion 111 toward the lower end portion 112. In addition, the first band body portion 140 configured to be disposed in the inter-finger portion fb located between the fingers of the patient extends from the upper end portion 111 side of the support member 110, and is configured to press the upper end portion 111 side of the support member 110 against the right hand H1 of the patient. Therefore, when the hemostasis is started in the state where the hemostatic device 100 is attached to the right hand H1 of the patient, the inflatable member 180 can apply a force to the upper end portion 111 of the support member 110. The upper end portion 111 side of the support member 110 is lifted by the force applied by the inflatable member 180. Accordingly, the support member 110 is disposed such that the lower surface 110*a* of the support member 110 is substantially parallel to the body surface of the right hand H1 of the patient. Therefore, in the hemostatic device 100, a compressive force of the inflatable member 180 can be directed in a direction perpendicular to the first puncture site p1 by securing the first band body portion 140 and the second band body portion 150 to the right hand H1 of the patient in a state where the inflatable member 180 and the support member 110 are disposed at the first puncture site p1. Accordingly, the hemostatic device 100 can effectively apply a compressive force to the first puncture site p1.

In addition, the support member 110 has an outer shape bilaterally symmetrical with respect to the long axis C of the first band body portion 140. That is, the outer shape of the support member 110 is bilaterally symmetric with respect to a plane containing the long axis C of the first band body portion 140 and perpendicular to the surfaces 110*a*, 110*b* of the support member 110.

In the hemostatic device 100 having the above configuration, since the support member 110 has the outer shape bilaterally symmetrical with respect to the long axis C of the first band body portion 140, a uniform tensile force can be applied to the support member 110 along the left-right direction by wrapping the band body portions 150 and 160 extending in the left-right direction based on the first band body portion 140 around the right hand H1 of the patient.

Accordingly, the hemostatic device 100 can prevent the positional deviation of the support member 110 in the state where the support member 110 is disposed on the right hand H1 of the patient.

In addition, the securing member 120 includes the third band body portion 160 extending in the third direction different from the first direction and the second direction. The third band body portion 160 extends in the third direction from the side surface portion 113 located on the side opposite to the second band body portion 150 with the support member 110 sandwiched therebetween. The third band body portion 160 includes: the one end portion 161 located on the support member 110 side; the other end portion 163 located on the side opposite to the one end portion 161; and the main body portion 165 extending between the one end portion 161 and the other end portion 163. The main body portion 165 includes the second securing site 172 configured to be attachable to and removable from the second band body portion 150. In the second securing site 172, the end portion located on the other end portion 163 side is branched into the plurality of portions 172*a* and 172*b*.

In the hemostatic device 100 configured as described above, when the third band body portion 160 is wrapped around the right hand H1 of the patient, by pulling the main body portion 165 using the one end portion 161 of the third band body portion 160 as a base point, the first branch portion 172*a* (or the second branch portion 172*b*) of the second securing site 172 not used for connecting the second band body portion 150 and the third band body portion 160 can be prevented from being lifted from the right hand H1 of the patient. In addition, when connecting the second band body portion 150 and the third band body portion 160, the operator can selectively connect the third securing site 173 disposed on the inner surface of the second band body portion 150 to the first branch portion 172*a* and the second branch portion 172*b*. Accordingly, when the hemostatic device 100 is attached to the right hand H1 of the patient, the hemostatic device 100 can narrow the range in which the band body portions 150 and 160 restrain the right hand H1 of the patient.

In addition, the corner portions 115*a*, 115*b*, and 115*c* located on the outer peripheral side surface of the support member 110 have the rounded shape.

Since the hemostatic device 100 has the above configuration, when the inflatable member 180 is inflated to apply a compressive force to the first puncture site p1, the hemostatic device 100 can prevent the corner portions 115*a*, 115*b*, and 115*c* of the support member 110 from biting into the right hand H1 of the patient.

The support member 110 has the hole 117 at a position overlapping the inflatable member 180.

Since the hemostatic device 100 has the above configuration, when the operator disposes the inflatable member

180 and the support member 110 in the first puncture site p1, the position of the marker portion 185 disposed in the inflatable member 180 can be visually confirmed through the hole 117 formed in the support member 110. Therefore, in the hemostatic device 100, the inflatable member 180 can be appropriately positioned at the first puncture site p1 based on the marker portion 185.

Next, a hemostatic device according to a modification of Embodiment 1 and a hemostatic device according to Embodiment 2 will be described. In the description below, features and aspects of the hemostatic device, the use procedure of the hemostatic device, and the like described in Embodiment 1 will not be repeated. In addition, contents that are not particularly described in the modification and Embodiment 2 may be the same as those in Embodiment 1.

<Modification>

A shape of the second securing site 172 disposed in the third band body portion 160 can be freely changed. For example, as illustrated in FIG. 18, the second securing site 172 may be configured in a heart shape in which two branch portions 172*a* and 172*b* are formed on the other end portion 163 side of the third band body portion 160.

Embodiment 2

Figure 19:
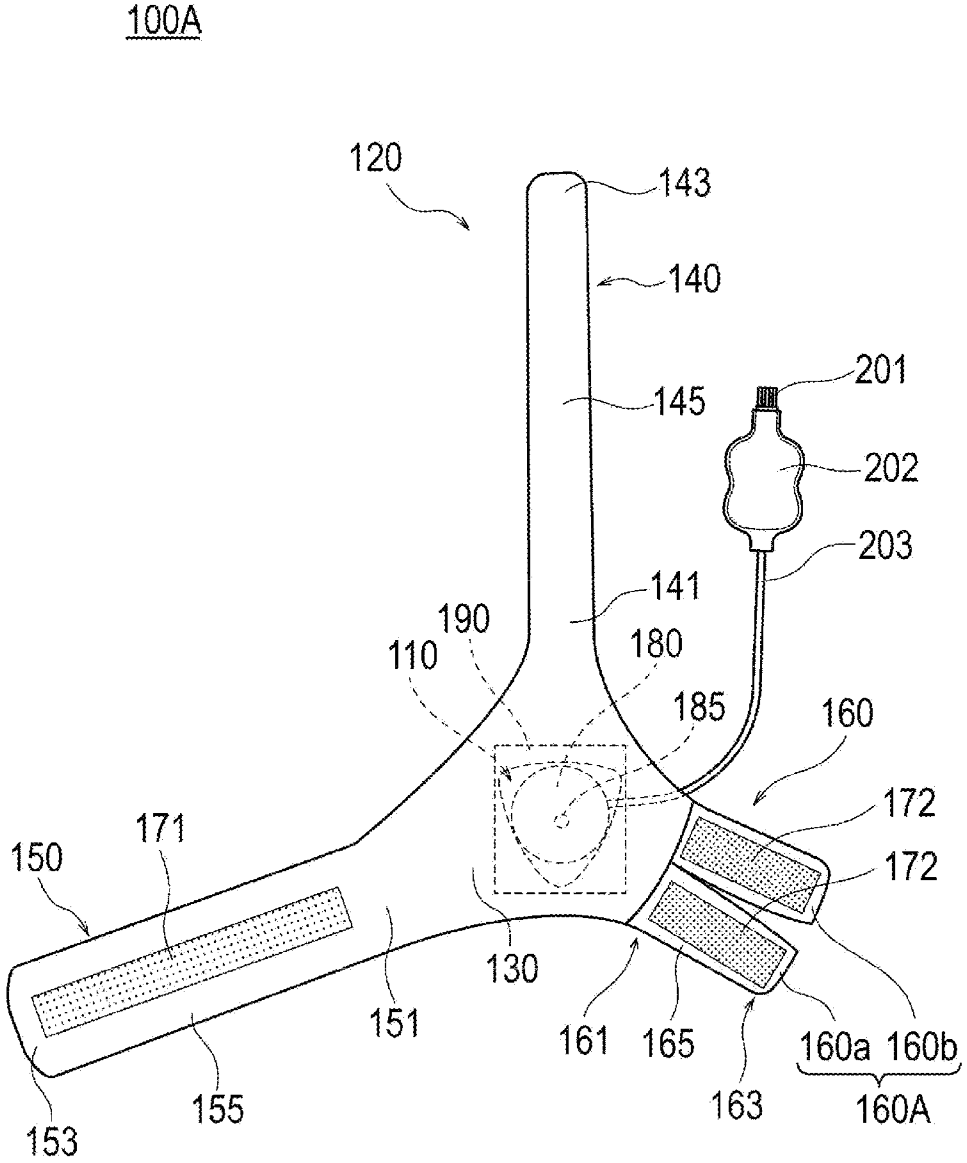
FIG. 19 is a plan view illustrating a hemostatic device according to Embodiment 2, viewed from an outer surface side of each band body portion.

As illustrated in FIG. 19, in a hemostatic device 100A according to Embodiment 2, the securing member 120 includes the third band body portion 160 extending in the third direction different from the first direction and the second direction.

The third band body portion 160 extends in the third direction from the side surface portion 113 (see FIG. 8) located on the side opposite to the second band body portion 150 with the support member 110 sandwiched therebetween.

The third band body portion 160 includes: the one end portion 161 located on the support member 110 side; the other end portion 163 located on the side opposite to the one end portion 161; and the main body portion 165 extending between the one end portion 161 and the other end portion 163.

The third band body portion 160 branches into a first portion 160*a* and a second portion 160*b* at the main body portion 165.

The second securing site 172 can be disposed in each of the first portion 160*a* and the second portion 160*b*.

In the hemostatic device 100A according to Embodiment 2, when connecting the second band body portion 150 and the third band body portion 160, the operator can selectively connect the third securing site 173 (see FIG. 2) disposed on the inner surface of the second band body portion 150 to the first portion 160*a* and the second portion 160*b*.

Accordingly, in the hemostatic device 100A according to Embodiment 2, similarly to the hemostatic device 100 according to Embodiment 1, when the hemostatic device 100A is attached to the hand H of the patient, the range in which the band body portions 150 and 160 restrain the right hand H1 of the patient can be narrowed.

<Modification of Support Member>

Hereinafter, the modification of the support member will be described with reference to FIGS. 20 to 24.

Figure 20:
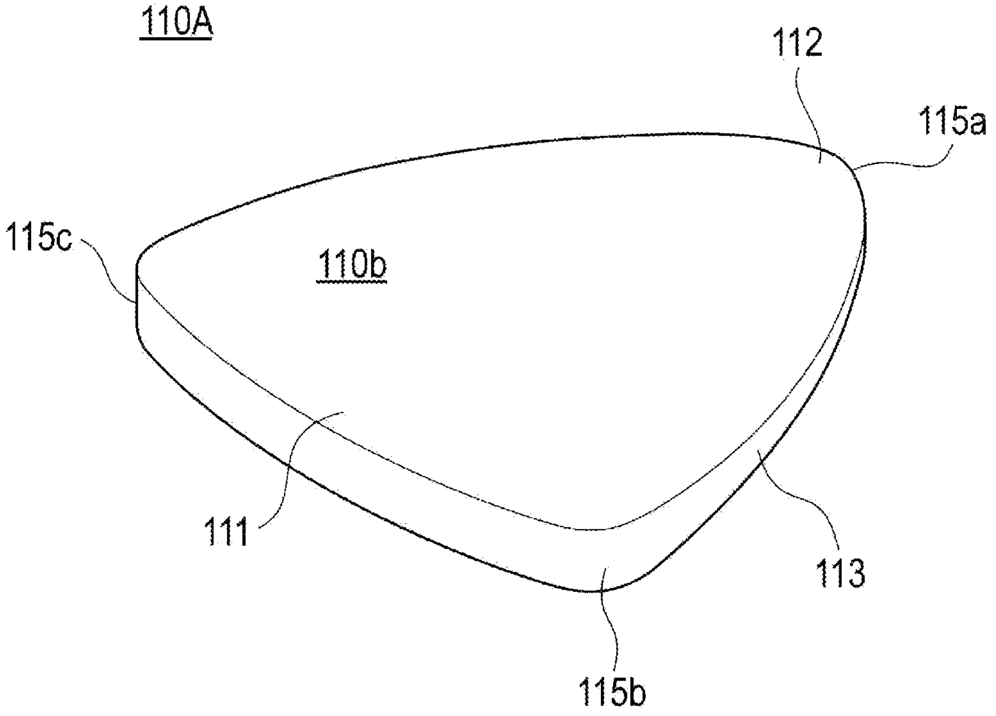
FIG. 20 is a view illustrating a modification of the support member.

As illustrated in FIG. 20, the hole 117 (see FIG. 7) is not formed in a support member 110A. As described above, the hole portion 117 may not be formed in the support member 110A. When the hole 117 is not provided as in the support member 110A, a portion of the support member 110A overlapping the marker portion 185 (see FIG. 6) or the entire support member 110A can be formed to be transparent.

Figure 21:
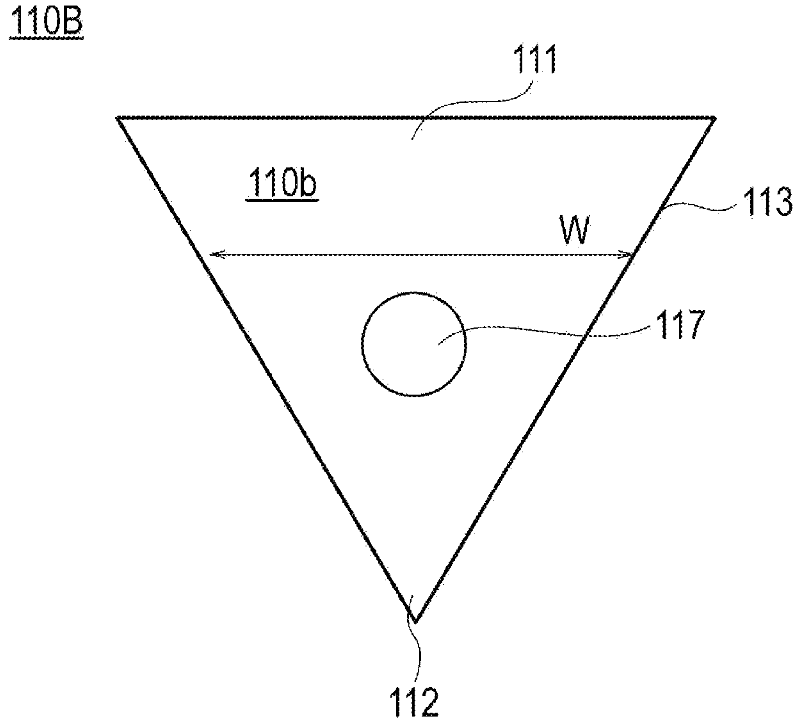
FIG. 21 is a view illustrating a modification relating to a shape of the support member.
Figure 22:
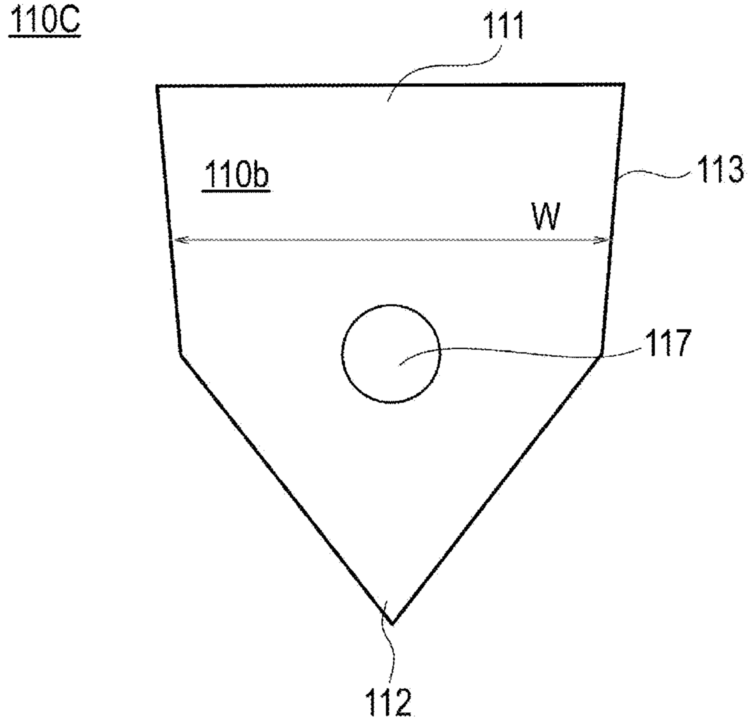
FIG. 22 is a view illustrating a modification relating to a shape of the support member.
Figure 23:
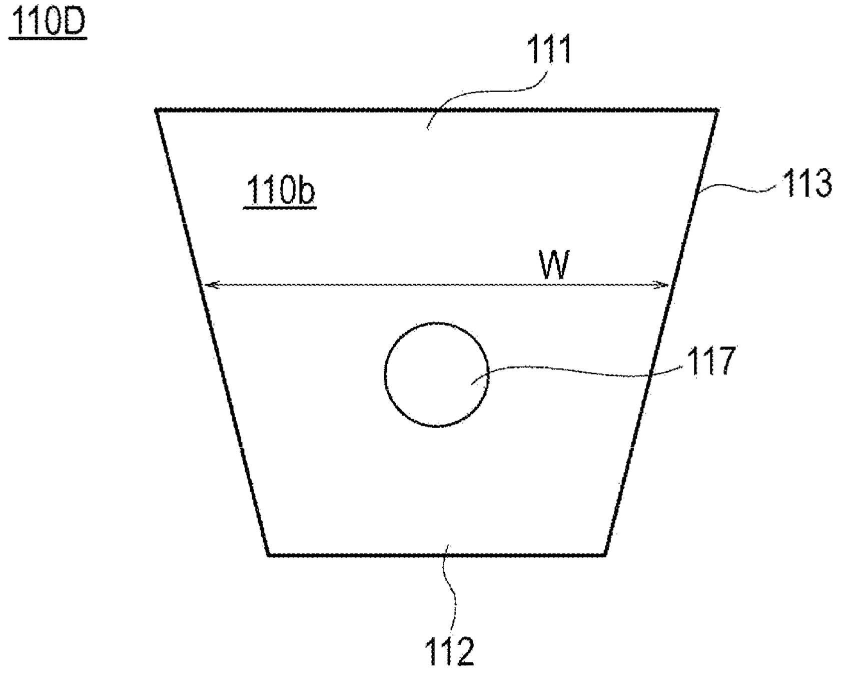
FIG. 23 is a view illustrating a modification relating to a shape of the support member.
Figure 24:
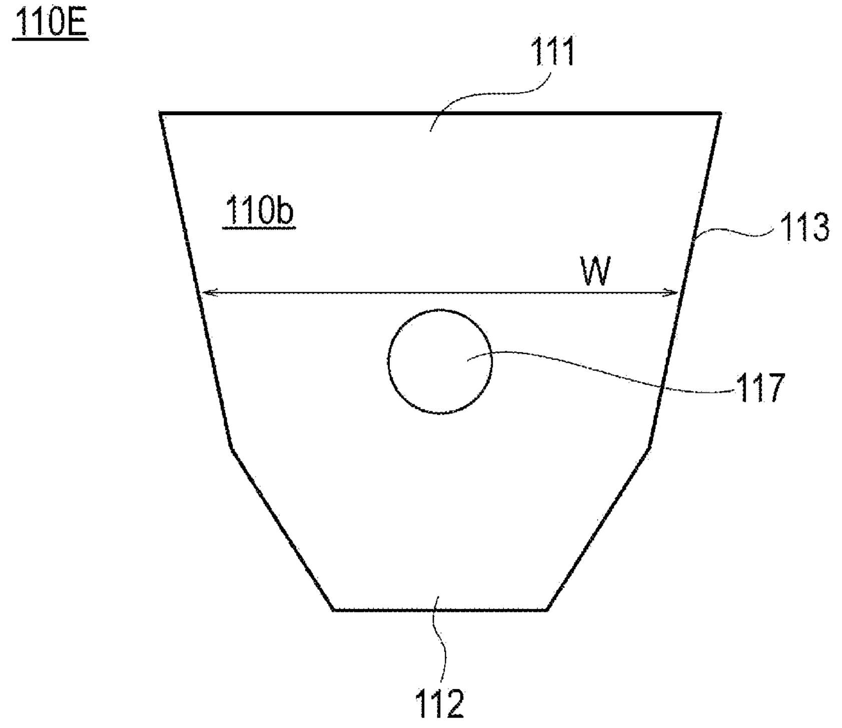
FIG. 24 is a view illustrating a modification relating to a shape of the support member.

As illustrated in FIGS. 21 to 24, a planar shape of the support member is not particularly limited as long as a width of the support member is formed to shorten from the upper end portion 111 toward the lower end portion 112. As illustrated in FIG. 21, a support member 110B may have a triangular shape in which corner portions are not formed in a rounded shape. As illustrated in FIG. 22, a support member 110C may have a pentagonal shape. As illustrated in FIG. 23, a support member 110D may have a trapezoidal shape. As illustrated in FIG. 24, a support member 110E may have a hexagonal shape.

In the support members 110B, 110C, 110D, and 110E illustrated in FIGS. 21 to 24, formation of the hole 117 may be omitted. The support members 110C, 110D, and 110E illustrated in FIGS. 22 to 24 may have rounded corner portions.

The shape, the dimension, and the like of each part of the hemostatic device are not particularly limited, and may be appropriately changed as long as the hemostasis can be performed on the puncture site by the compress of the pressing member disposed at the puncture site.

The detailed description above describes embodiments of a hemostatic device and operational use representing examples of the new hemostatic device and method of use disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST

100, 100A hemostatic device
110, 110A, 110B, 110C, 110D, 110E support member
110*a* lower surface of support member
110*b* upper surface of support member
111 upper end portion of support member
112 lower end portion of support member
113 side surface portion of support member
115*a*, 115*b*, 115*c* corner portion of support member
120 securing member
130 covering portion
130*a* inner surface of covering portion
130*b* outer surface of covering portion
140 first band body portion
141 one end portion of first band body portion
143 other end portion of first band body portion
145 main body portion of first band body portion
150 second band body portion
151 one end portion of second band body portion
153 other end portion of second band body portion
155 main body portion of second band body portion
160 third band body portion
160*a* first portion
160*b* second portion
161 one end portion of third band body portion
163 other end portion of third band body portion
165 main body portion of third band body portion
171 first securing site
172 second securing site
172*a* first branch portion
172*b* second branch portion
173 third securing site
174 fourth securing site

180 inflatable member (pressing member)
183 lumen of inflatable member
185 marker portion
190 connection member
191 space
A forearm
B1 metacarpal bone of index finger
B2 metacarpal bone of thumb
C long axis of first band body portion
H hand
H1 right hand
H2 left hand
T1 extensor pollicis longus muscle tendon
T2 extensor pollicis brevis muscle tendon
V1 blood vessel (distal radial artery)
V2 artery
fb inter-finger portion
p1 first puncture site
p2 second puncture site
p3 third puncture site
p4 fourth puncture site

What is claimed is:

1. A hemostatic device, comprising:
a support member configured to cover a puncture site in a patient;
a securing member configured to secure the support member to the puncture site of the patient;
a pressing member connected to the support member and configured to compress the puncture site of the patient, the pressing member possessing a rigidity;
the support member including an upper end portion that is located on a distal side of the pressing member and forms an end portion of the support member, a lower end portion that is located on a proximal side of the pressing member and forms an end portion on a side opposite to the upper end portion, and a side surface portion that connects the upper end portion and the lower end portion, the support member possessing a rigidity higher than the rigidity of the pressing member, the support member possessing a width, the side surface portion possessing a thickness;
the securing member including a first band body portion configured to be disposed between fingers of the patient and extending in a first direction, and a second band body portion extending in a second direction different from the first direction;
the support member being configured such that the width of the support member becomes shorter from the upper end portion toward the lower end portion and the thickness of the side surface portion becoming thinner from the upper end portion toward the lower end portion;
the first band body portion extending in the first direction away from the upper end portion side; and
the second band body portion extending in the second direction away from the side surface portion side.

2. The hemostatic device according to claim 1, wherein the first band body portion has an axis that extends along a length of the first band body portion, the support member having an outer shape bilaterally symmetrical with respect to the axis of the first band body portion.

3. The hemostatic device according to claim 1, wherein
the securing member includes a third band body portion extending in a third direction different from the first direction and the second direction,
the third band body portion extends in the third direction from the side surface portion located on a side opposite to the second band body portion with the support member located therebetween,
the third band body portion including one end portion located on the support member side, an other end portion located on a side opposite to the one end portion, and a main body portion extending between the one end portion of the third band body portion and the other end portion of the third band body portion,
the main body portion of the third band body portion including a securing site configured to be attachable to and removable from the second band body portion, and
in the securing site, an end portion located on the other end portion side is branched into a plurality of portions.

4. The hemostatic device according to claim 1, wherein
the securing member includes a third band body portion extending in a third direction different from the first direction and the second direction,
the third band body portion extends in the third direction from the side surface portion located on a side opposite to the second band body portion with the support member located therebetween,
the third band body portion including one end portion located on the support member side, an other end portion located on a side opposite to the one end portion, and a main body portion extending between the one end portion of the third band body portion and the other end portion of the third band body portion, and
the third band body portion is branched at the main body portion.

5. The hemostatic device according to claim 1, wherein corner portions located on an outer peripheral side surface of the support member have a rounded shape.

6. The hemostatic device according to claim 1, wherein the support member has a hole at a position overlapping the pressing member.

7. A hemostatic device securable to a hand of a patient, the hemostatic device comprising:
a covering portion positionable in overlying relation to a puncture site on the hand of the patient when the hemostatic device is secured to the hand of the patient, the covering portion including an inner surface configured to face toward the patient's hand when the hemostatic device is secured to the hand of the patient;
a first band body portion and a second band body portion for securing the covering portion to the patient's hand;
the first band body portion being fixed to the covering portion, extending away from a first part of the covering portion in a first direction of extent and configured to be positioned between fingers of the patient's hand;
the second band body portion being fixed to the covering portion and extending away from a second part of the covering portion in a second direction of extent different from the first direction of extent, the first part of the covering portion being spaced from the second part of the covering portion;
a pressing member that is expandable to apply a compressive force to the puncture site when the hemostatic device is secured to the hand of the patient, the covering portion overlying the pressing member;
a support member positioned between the covering portion and the pressing member so that the covering portion overlies the support member and the support member overlies the pressing member, the support member being more rigid than the pressing member;
the support member including a first end portion and a second end portion that are disposed at opposite sides of the support member in a plan view of the support member, the first end portion of the support member facing towards the first part of the covering portion and being located closer to the first part of the covering portion than the second end portion of the support member, the second end portion of the support member facing away from the first part of the covering portion; and the support member possessing a thickness, the thickness of the first end portion of the support member being greater than the thickness of the second end portion of the support member.

8. The hemostatic device according to claim 7, wherein the support member possesses a width, the width of the first end portion of the support member being greater than the width of the second end portion of the support member.

9. The hemostatic device according to claim 7, wherein a central portion of the support member as seen in a plan view includes a through hole.

10. The hemostatic device according to claim 7, wherein at least a central part of the covering portion and at least a central part of the support member are transparent.

11. The hemostatic device according to claim 7, wherein a part of the expandable pressing member includes a marker that is viewable to align the expandable pressing member with the puncture site.

12. The hemostatic device according to claim 11, wherein at least a central part of the covering portion, at least a central part of the support member and the part of the expandable pressing member are transparent.

13. The hemostatic device according to claim 7, further comprising a third band body portion fixed to the covering portion and extending away from a third part of the covering portion in a third direction of extent, the third part of the covering portion being spaced from the first and second parts of the covering portion, the third direction of extent being different from the first and second directions of extent.

14. The hemostatic device according to claim 13, wherein the first band body portion, the second band body portion and the third band body portion each includes a first surface and a second surface that face in opposite directions, the first surfaces of the first band body portion, the second band body portion and the third band body portion facing in a common direction when the hemostatic device is laid flat, the second surfaces of the first band body portion, the second band body portion and the third band body portion facing in a common direction when the hemostatic device is laid flat, the first surface of the first band body portion and the second surface of the second band body portion each including a securing portion that mate with one another to connect the first band body portion and the second band body portion to each other, the first surface of the second band body portion and the second surface of the third band body portion each including a securing portion that mate with one another to connect the second band body portion and the third band body portion to each other.

15. The hemostatic device according to claim 13, wherein the second band body portion and the third band body portion each includes a first surface and a second surface that face in opposite directions, the first surfaces of the second band body portion and the third band body portion facing in a common direction when the hemostatic device is laid flat, the second surfaces of the second band body portion and the third band body portion facing in a common direction when the hemostatic device is laid flat, the first surface of the second band body portion and the second surface of the third band body portion each including a securing portion that mate with one another to connect the second band body portion and the third band body portion to each other, the securing portion on the second surface of the third band body portion including first and second branch portions of the securing portion that are spaced apart from one another along at least a portion of a longitudinal extent of the first and second branch portions of the securing portion.

16. The hemostatic device according to claim 7, further comprising a connection member directly fixed to the inner surface of the covering portion, the connection member including a surface facing the inner surface of the covering portion, the support member being positioned between the surface of the connection member and the inner surface of the covering portion.

17. The hemostatic device according to claim 16, wherein the surface of the connection member is a first surface, the connection member including a second surface opposite the first surface, the pressing member being secured to the second surface of the connecting member.

18. The hemostatic device according to claim 7, further comprising a tube in fluid communication with an interior of the expandable pressing member to introduce a fluid into the interior of the pressing member to expand the pressing member.

19. A method comprising:

positioning an expandable pressing member of a hemostatic device on a patient's hand; a covering portion being positioned in overlying relation to the pressing member with a first band body portion fixed to and extending away from a first part of the covering portion in a first direction of extent, a second band body portion fixed to and extending away from a second part of the covering portion in a second direction of extent and a third band body portion fixed to the covering portion and extending away from the covering portion, the first part of the covering portion being spaced from the second part of the covering portion; a support member positioned between the covering portion and the pressing member so that the covering portion overlies the support member and the support member overlies the pressing member, the support member being more rigid than the pressing member, the support member including a first end portion and a second end portion that are disposed at opposite sides of the support member in a plan view of the support member, the first end portion of the support member facing towards the first part of the covering portion and being located closer to the first part of the covering portion than the second end portion of the support member, the second end portion of the support member facing away from the first part of the covering portion, the support member possessing a thickness, the thickness of the first end portion of the support member being greater than the thickness of the second end portion of the support member; the first band body portion, the second band body portion and the third band body portion each including a first surface and a second surface that face in opposite directions, the first surfaces of the first band body portion, the second band body portion and the third band body portion facing in a common direction when the hemostatic device is laid flat, the second surfaces of the first band body portion, the second band body portion and the third band body portion facing in a common direction when the hemostatic device is laid flat; the first surface of the first band body portion and the first surface of the second band body portion each including a securing portion; the second surface of the second band body portion and the second surface of the third band body portion each including a securing portion; the securing portion on the second surface of the third band body portion including first and second branch portions that are spaced apart from one another along at least a portion of a longitudinal extent of the first and second branch portions of the securing portion;

positioning the pressing member in overlaying relation to either a first puncture site of the patient's hand or a second puncture site of the patient's hand, the second puncture site being spaced from the first puncture site;

securing the pressing member and the covering portion to the patient's hand;

the securing of the pressing member and the covering portion to the patient's hand comprising:

wrapping the third band body portion and the second band body portion around a portion of the patient's hand and mating the securing portion on the first surface of the second band body portion with the first branch portion of the securing portion on the second surface of the third band body portion when the pressing member is positioned in overlaying relation to the first puncture site of the patient's hand, or wrapping the third band body portion and the second band body portion around a portion of the patient's hand and mating the securing portion on the first surface of the second band body portion with the second branch portion of the securing portion on the second surface of the third band body portion when the pressing member is positioned in overlaying relation to the second puncture site of the patient's hand; and positioning the first band body portion between two fingers of the patient's hand and mating the securing portion on the first surface of the first band body portion with the securing portion on the second surface of the second band body portion.

20. The method according to claim 19, further comprising introducing fluid into an interior of the expandable pressing member while a support member is located between the covering portion and the pressing member.

* * * * *